US008889949B2

(12) United States Patent
Wu et al.

(10) Patent No.: US 8,889,949 B2
(45) Date of Patent: Nov. 18, 2014

(54) METHOD FOR INCREASING RESISTANCE OF MONOCOT PLANTS AGAINST ABIOTIC STRESSES, TPSP FUSION ENZYME GENE CONSTRUCTS, AND TRANSFORMANTS

(75) Inventors: Ray J. Wu, Ithaca, NY (US); Ajay K. Garg, Ithaca, NY (US); Ju-Kon Kim, SungNam (KR); Baek-Hie Nahm, Kyungki (KR); Yang-Do Choi, Seoul (KR); In-Cheol Jang, Kyungki (KR); Won-Bin Choi, Seoul (KR); Yeon-Seak Kim, Kyungki (KR); Chung-Ho Kim, Chungbuk (KR); Sang-Ik Song, Kyungki (KR)

(73) Assignees: Cornell Research Foundation, Inc., Ithaca, NY (US); Myongji University Industry and Academia Cooperation Foundation, Yongin-Si, Gyeonggi-Do (KR)

( * ) Notice: Subject to any disclaimer, the term of this patent is extended or adjusted under 35 U.S.C. 154(b) by 1445 days.

(21) Appl. No.: 11/619,335

(22) Filed: Jan. 3, 2007

(65) Prior Publication Data
US 2008/0034452 A1 Feb. 7, 2008

Related U.S. Application Data

(63) Continuation-in-part of application No. 11/353,099, filed on Feb. 14, 2006, now abandoned, which is a continuation of application No. 10/324,058, filed on Dec. 20, 2002, now abandoned, said application No. 11/619,335 is a continuation-in-part of application No. 10/700,201, filed on Nov. 3, 2003, now abandoned.

(60) Provisional application No. 60/424,410, filed on Nov. 6, 2002, provisional application No. 60/430,861, filed on Dec. 4, 2002.

(30) Foreign Application Priority Data

Jun. 20, 2002 (KR) .................. 10-2002-0034695

(51) Int. Cl.
*A01H 1/00* (2006.01)
*A01H 5/10* (2006.01)
*C12N 5/04* (2006.01)
*C12N 15/82* (2006.01)
*C12N 15/87* (2006.01)
*C12P 21/04* (2006.01)
*C12N 9/16* (2006.01)
*C12N 9/10* (2006.01)

(52) U.S. Cl.
CPC ..... *C12Y 204/01015* (2013.01); *C12N 15/8273* (2013.01); *C12N 9/16* (2013.01); *C12Y 301/03012* (2013.01); *C12N 9/1051* (2013.01); *C07K 2319/00* (2013.01)
USPC ........... 800/284; 800/289; 800/294; 800/298; 800/320.1; 435/69.7; 435/424; 435/469

(58) Field of Classification Search
None
See application file for complete search history.

(56) References Cited

U.S. PATENT DOCUMENTS

| 5,273,894 | A | 12/1993 | Strauch et al. |
| 5,276,268 | A | 1/1994 | Strauch et al. |
| 5,352,605 | A | 10/1994 | Fraley et al. |
| 5,591,616 | A | 1/1997 | Hiei et al. |
| 5,637,489 | A | 6/1997 | Strauch et al. |
| 5,641,876 | A | 6/1997 | McElroy et al. |
| 5,684,239 | A | 11/1997 | Wu et al. |
| 5,981,842 | A | 11/1999 | Wu et al. |
| 6,130,368 | A | 10/2000 | Londesborough et al. |
| 6,133,034 | A | 10/2000 | Strom et al. |
| 6,174,724 | B1 | 1/2001 | Rogers et al. |
| 6,323,001 | B1 | 11/2001 | Londesborough et al. |
| 6,429,357 | B1 | 8/2002 | McElroy et al. |
| 6,833,490 | B1 | 12/2004 | Goddijn et al. |
| 2003/0009784 | A1 | 1/2003 | Lebel et al. |

FOREIGN PATENT DOCUMENTS

| WO | WO 96/00789 A1 | 1/1996 | |
| WO | WO 97/26365 | 7/1997 | |
| WO | WO 99/46370 A2 | 9/1999 | |
| WO | WO9946370 | * 9/1999 | ............. C12N 15/00 |
| WO | WO 99/66785 A1 | 12/1999 | |
| WO | WO 00/00601 A2 | 1/2000 | |
| WO | WO 00/22141 A2 | 4/2000 | |
| WO | WO 00/70067 A1 | 11/2000 | |
| WO | WO 01/64850 A1 | 9/2001 | |

OTHER PUBLICATIONS

Su et al 1998 Plant Physiology 117:913-922, provided in Applicant's IDS.*

(Continued)

*Primary Examiner* — Brent T Page
*Assistant Examiner* — Matthew Keogh
(74) *Attorney, Agent, or Firm* — LeClairRyan, a Professional Corporation

(57) ABSTRACT

The present invention relates to a method for increasing resistance of monocot plants against abiotic stress which comprises a step of transforming monocot plants with a recombinant plasmid containing a fused gene (TPSP) of trehalose-6-phosphate synthetase (TPS) gene and trehalose-6-phosphate phosphatase (TPP) gene to express the TPSP gene while maintaining normal growth and development characteristics. The present invention can increase the resistance of monocot plants against various stresses so that it can greatly contribute to the improvement of production and quality of valuable agricultural crops. The present invention also relates to a transgenic monocot plant, plant cell, or protoplast transformed with a nucleic acid encoding an enzyme for trehalose biosynthesis, under control of an inducible promoter, that increases tolerance to low temperature, salt, and water stress.

32 Claims, 15 Drawing Sheets

(56) References Cited

OTHER PUBLICATIONS

Seo et al 2000 Applied and Environmental Microbiology 66:6 p. 2484-2490.*

Su et al 1998 Plant Physiology 117: p. 913-922.*

Almeida et al., "Genetic Engineering of Maize Towards Desiccation Tolerance: Electroporation with the Trehalose Gene," *Genetika* 35(2):111-121 (2003).

Garg et al., "Trehalose Accumulation in Rice Plants Confers High Tolerance Levels to Different Abiotic Stresses," *PNAS* 99(25):15898-15903 (2002).

Goddijn et al., "Inhibition of Trehalase Activity Enhances Trehalose Accumulation in Transgenic Plants," *Plant Physiology* 113:181-190 (1997).

Goodijn et al., "Trehalose Metabolism in Plants," *Elsevier Science* 4(8):315-319 (1999).

Goodijn et al., "Trehalose Metabolism in Plants," *Trends in Plant Science* 4(8):315-319 (1999).

Holmstrom et al., "Drought Tolerance in Tobacco," *Nature* 379:683-684 (1996).

Jang et al., "Expression of a Bifunctional Fusion of the *Escherichia coli* Genes for Trehalose-6-Phosphate Phosphatase in Transgenic Rice Plants Increase Trehalose Accumulation and Abiotic Stress Tolerance without Stunting Growth," *Plant Physiology* 131(2):516-524 (2003).

Jang et al., "Subcellular Targeting of Green Fluorescent Protein to Plastids in Transgenic Rice Plants Provides a High-Level Expression Systems," *Molecular Breeding* 5:453-461 (1999).

Nuccio et al., "Metabolic Engineering of Plants for Osmotic Stress Resistance," *Current Opinion in Plant Biotechnology* 2:128-134 (1999).

Penna et al., "Building Stress Tolerance Through Over-Producing Trehalose in Transgenic Plants," *Trends in Plant Science* 8(8):355-357 (2003).

Pilon-Smits et al., "Trehalose-Producing Transgenic Tobacco Plants Show Improved Growth Performance Under Drought Stress," *Journal of Plant Physiology* 152:525-532 (1998).

Romero et al., "Expression of the Yeast *Trehalose-6-Phosphate Synthase* Gene in Transgenic Tabacco Plants: Pleiotropic Phenotypes Include Drought Tolerance," *Planta* 201:293-297 (1997).

Rontein et al., "Metabolic Engineering of Osmoprotectant Accumulation in Plants," *Metabolic Engineering* 4:49-59 (2002).

Sakamoto et al., "Metabolic Engineering of Rice Leading to Biosynthesis of Glycinebetaine and Tolerance to Salt and Cold," *Plant Molecular Biology* 38:1011-1019 (1998).

Seo et al., "Characterization of a Bifunctional Enzyme Fusion of Trehalose-6-Phosphate Synthetase and Trehalose-6-Phosphate Phosphatase of *Escherichia coli*," *Applied and Environmental Microbiology* 66(6):2484-2490 (2000).

Su et al., "Dehydration-Stress-Regulated Transgene Expression in Stably Transformed Rice Plants," *Plant Physiology* 117(3):913-922 (1998).

Vogel et al., "Trehalose-6-Phosphate Phosphatases from *Arabidopsis thaliana*: Identification by Functional Complementation of the Yeast *tps2* Mutant," *The Plant Journal* 13(5):673-683 (1998).

Xiuyu et al., "Expression of *otsA* Gene In Tobacco and Improvement Sress Tolerance," *Acta Microbiologica Sinica* 41(4):427-431 (2001) (English Abstract).

* cited by examiner pSB109-TPSP

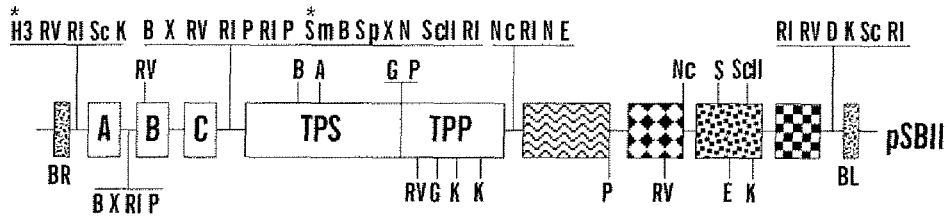

pSB-RTSP

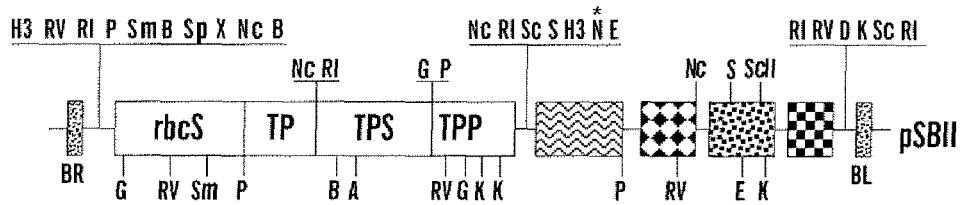

A: AccI, B: BamHI, C: ClaI, D: DraI, E: EagI, G: BglII, H3: HindIII, K: KpnI,
N: NotI, Nc: NcoI, P: PstI, RI: EcoRI, RV: EcoRV, Sc: SacI, ScII: SacII,
Sm: SmaI, Sp: SpeI, St: SstI, X: XbaI R.E. WITH STAR (*) ARE UNIQUE SITES

| A | 4ABRCI OF BARLEY HVA22 (0.18kb) |
| B | Rice *ActI* BASAL PROMOTER (0.18kb) |
| C | INTRON1-EXON2-INTRON 2 of HVA22 (0.24kb) |
| | 35S PROMOTER (0.74kb) |
| rbcS | Rice *rbcS* PROMOTER (1.3kb) |
| Tp | Rice *rbcS* TRANSIT PEPTIDE (0.16kb) |
| TPS TPP | *E. coli* TREHALOSE-6-PHOSPHATE SYNTHASE/PHOSPHATASE (2.2 kb) |
| | BAR CODING REGION (0.59kb) |
| | 3' *PinII* TERMINATOR (1.0kb) |
| | 3' *NOS* TERMINATOR (0.28kb) |

*FIG. 5C*

SEQUENCE LISTING

```
<160> NUMBER OF SEQ ID NOS: 2

<210> SEQ ID NO 1
<211> LENGTH: 36
<212> TYPE: DNA
<213> ORGANISM: Artificial
<220> FEATURE:
<223> OTHER INFORMATION: Fusion segment

<400> SEQUENCE: 1
ccaaagctag ggtcgagatc tgcagagctt atgaca                         36

<210> SEQ ID NO 2
<211> LENGTH: 8
<212> TYPE: PRT
<213> ORGANISM: Artificial
<220> FEATURE:
<223> OTHER INFORMATION: Fusion segment

<400> SEQUENCE: 2

Leu Gly Ser Arg Ser Ala Glu Leu
1               5
```

METHOD FOR INCREASING RESISTANCE OF MONOCOT PLANTS AGAINST ABIOTIC STRESSES, TPSP FUSION ENZYME GENE CONSTRUCTS, AND TRANSFORMANTS

This application is a continuation-in-part application of U.S. patent application Ser. No. 11/353,099, filed Feb. 14, 2006, which is a continuation of U.S. patent application Ser. No. 10/324,058, filed Dec. 20, 2002, now abandoned, which claims priority from Korean Patent Application Serial No. 10-2002-0034695, filed Jun. 20, 2002. All of these applications are hereby incorporated by reference in their entirety.

This application is also a continuation-in-part application of U.S. patent application Ser. No. 10/700,201, filed Nov. 3, 2003, which claims the benefit of U.S. Provisional Patent Application Ser. No. 60/424,410, filed Nov. 6, 2002, and U.S. Provisional Patent Application Ser. No. 60/430,861, filed Dec. 4, 2002. All of these applications are hereby incorporated by reference in their entirety.

FIELD OF THE INVENTION

The present invention relates to a method for increasing the resistance of monocot plants against abiotic stress. More specifically, the present invention relates to a method for increasing the resistance of monocot plants against abiotic stress by expressing trehalose-6-phosphate synthetase (TPS) and trehalose-6-phosphate phosphatase (TPP) in monocot plants while surprisingly maintaining normal growth and development characteristics. The present invention also relates to transgenic monocot plants which are transformed with a nucleic acid encoding an enzyme in the trehalose biosynthetic pathway to increase tolerance to low temperature stress, water stress, and salt stress.

BACKGROUND OF THE INVENTION

International Publication WO 00/70067, published Nov. 23, 2000, is directed to a rice actin 2 promoter and actin 2 intron and methods for the use thereof. Environment or stress resistance to drought (see corresponding U.S. Pat. No. 6,429,357, at cols. 19 and 20) is described by introducing genes encoding for trehalose-6-phosphate synthase and through subsequent action of native phosphatases in the cell or by introduction and coexpression of a specific phosphatase resulting in trehalose which is a protective compound able to mitigate the effects of stress.

U.S. Pat. No. 5,925,804 is directed to the increase in the production of Trehalsoe in plants using an *E. coli* trehalose phosphate synthase gene, see cols. 7 and 8.

Seo H S at al., *Appl Environ. Microbiol*, 65:2484-2490, (2000), which relates to the characterization of a bifunctional fusion enzyme (TPSP) of trehalose-6-phosphate synthetase and trehalose-6-phosphate phophatase of *Escherichia coli*.

Trehalose (α-D-glucopyranosyl-[1,1]-α-D-glucopyranose) is a non-reducing diglucoside and therefore does not react with amino acids or proteins as part of Maillard browning. Trehalose is found in various organisms, including bacteria, algae, fungi, yeast, insects and some plants, and serves not only as a carbohydrate reservoir but also as a protective agent against a variety of physical and chemical stresses (see, Elbein A, *Adv. Carbohydr. Chem. Biochem.*, 30:227-256, 1974; Eleutherio E C A et al., *Cryobiology*, 30:591-596, 1993; Strom A R and Kaasen I, *Mol. Microbiol.*, 8:205-210, 1993; van Laere A, *FEMS Microbiol. Rev.*, 63:201-210, 1989; and Wiemken A, *J. Gen, Microbiol.*, 58:209-217, 1990). Further, it has been known that trehalose shows a high water-retention activity under dry conditions to maintain the fluidity of the cell membranes and allow the plant to have a resistance against naturally occurring stresses during cycles of dehydration and rehydration (see, Leslie S B et al., *Appl. Environ. Microbiol.*, 61:3592-3597, 1995; Drennan P M et al., *J. Plant Physiol.*, 142:493-496, 1993; and Muller J et al., *Plant Sci.*, 112:1-9, 1995). Such effect of trehalose on stress resistance has been demonstrated for cryptobiotic plant species such as *S. leidophylla* having resistance against dehydration. In this regard, it has been reported that trehalose accumulates to the level of 12% of plant dry weight during dehydration of such plant species, whereas trehalose accumulation is reduced during rehydration (see, Goddijn O J M and van Dun K, *Trends Plant Sci.*, 4:315-319, 1999).

By virtue of such activity of trehalose, it has been attempted to increase stress resistance of plants. Up to the present, transgenic plants that express trehalose-6-phosphate synthetase (PTS) gene and/or trehalose-6-phosphate phosphatase (TPP) gene from *E. coli* or yeast in dicotyledon plants have been found. These transgenic plants express trehalose generally at a very low level. However, in these transgenic plants, although the stress resistance was somewhat increased, adverse effects appeared such as severe growth disturbance and warped roots. These adverse effects were exhibited even in the absence of trehalose accumulation (see, Holmstrom K-O et al., *Nature*, 379:683-684, 1996; Goddijn O J M et al., *Plant Physiol*, 113:181-1990, 1997; Muller et al., *Plant Sci*, 147:37-47, 1999; Pilon-Smits E A H et al., *J. Plant Physiol.*, 152:525-532, 1998; and Romeo C et al., *Planta*, 201:293-297, 1997).

In the production of food for human welfare and existence, monocot plants, including rice, barley, wheat, maize, etc., are regarded as being commercially valuable plants. Therefore, a lot of effort has been exerted to increase the productivity and quality of such crops. Particularly, continuous efforts have been made in order to produce crops having resistance against abiotic natural conditions, such as drought, an increase in salt concentration, low temperature, etc.

The explosive increase in world population, along with the continuing deterioration of arable land, scarcity of fresh water, and increasing environmental stress pose serious threats to global agricultural production and food security. Despite focused efforts to improve major crops for resistance to abiotic stresses such as drought, excessive salinity, and low temperature by traditional breeding, success has been limited (Boyer, J. S., "Plant Productivity and Environment," *Science*, 218:443-448 (1982)). This lack of desirable progress is attributable to the fact that tolerance to abiotic stress is a complex trait that is influenced by coordinated and differential expression of a network of genes. Fortunately, it is now possible to use transgenic approaches to improve abiotic stress tolerance in agriculturally important crops with far fewer target traits than had been anticipated (Zhang et al., "Engineering Salt-Tolerant *Brassica* Plants: Characterization of Yield and Seed Oil Quality in Transgenic Plants with Increased Vacuolar Sodium Accumulation," *Proc. Natl. Acad. Sci. USA*, 98:12832-12836 (2001)).

Abiotic stresses can directly or indirectly affect the physiological status of an organism by altering its metabolism, growth, and development. A common response of organisms to drought, salinity, and low-temperature stresses is the accumulation of sugars and other compatible solutes (Hare et al., "Dissecting the Roles of Osmolyte Accumulation During Stress," *Plant Cell Environ.*, 21:535-553 (1998)). These compounds serve as osmoprotectants and, in some cases, stabilize biomolecules under stress conditions (Hare et al., "Dissecting the Roles of Osmolyte Accumulation During Stress," *Plant*

*Cell Environ.*, 21:535-553 (1998); Yancey et al., "Living with Water Stress: Evolution of Osmolyte Systems," *Science,* 217: 1214-1222 (1982)). One such compound is trehalose, a non-reducing disaccharideof glucose, which plays an important physiological role as an abiotic stress protectant in a large number of organisms, including bacteria, yeast, and invertebrates (Crowe et al., "Anhydrobiosis," *Annu. Rev. Physiol.*, 54:579-599 (1992)). Trehalose has been shown to stabilize dehydrated enzymes, proteins, and lipid membranes efficiently, as well as protect biological structures from damage during desiccation. In the plant kingdom, most species do not seem to accumulate detectable amounts of trehalose, with the notable exception of the highly desiccation-tolerant "resurrection plants" (Wingler, "The Function of Trehalose Biosynthesis in Plants," *Phytochemistry,* 60:437-440 (2002)). The recent discovery of homologous genes for trehalose biosynthesis in *Selaginella lepidophylla, Arabidopsis thaliana*, and several crop plants suggests that the ability to synthesize trehalose may be widely distributed in the plant kingdom (Goddijn et al., "Trehalose Metabolism in Plants," *Trends Plant Sci.*, 4:315-319 (1999)). A putative plant gene for trehalose-6-phosphate synthase (TPS) can complement a Δtps1 mutant yeast strain, suggesting that the plant and yeast gene products are functionally similar (Zentella et al., "A *Selaginella lepidophylla* Trehalose-6-Phosphate Synthase Complements Growth and Stress-Tolerance Defects in a Yeast tps1 Mutant," *Plant Physiol.*, 119:1473-1482 (1999)).

In bacteria and yeast, trehalose is synthesized in a two-step process: trehalose-6-phosphate is first formed from UDP-glucose and glucose-6-phosphate in a reaction catalyzed by TPS. Trehalose-6-phosphate is then converted to trehalose by trehalose-6-phosphate phosphatase (TPP) (Goddijn et al., "Trehalose Metabolism in Plants," *Trends Plant Sci.*, 4:315-319 (1999)). Metabolic engineering for enhanced accumulation of trehalose in plants has been the recent focus of attention in some model dicot plants (Holmstrom et al., "Drought Tolerance in Tobacco," *Nature,* 379:683-684 (1996); Goddijn et al., "Inhibition of Trehalase Activity Enhances Trehalose Accumulation in Transgenic Plants," *Plant Physiol.*, 113: 181-190 (1997); Romero et al., "Expression of the Yeast Trehalose-6-Phosphate Synthase Gene in Transgenic Tobacco Plants: Pleiotropic Phenotypes Include Drought Tolerance," *Planta,* 201:293-297 (1997); Pilon-Smits et al., "Trehalose-Producing Transgenic Tobacco Plants Show Improved Growth Performance Under Drought Stress," *J. Plant Physiol.*, 152:525-532 (1998)). However, in these previous studies, constitutive overexpression of TPS and/or TPP genes from yeast or *Escherichia coli* in tobacco or potato plants resulted in undesirable pleiotropic effects, including stunted growth and altered metabolism under normal growth conditions (Goddijn et al., "Inhibition of Trehalase Activity Enhances Trehalose Accumulation in Transgenic Plants," *Plant Physiol.*, 113:181-190 (1997); Romero et al., "Expression of the Yeast Trehalose-6-Phosphate Synthase Gene in Transgenic Tobacco Plants: Pleiotropic Phenotypes Include Drought Tolerance," *Planta,* 201:293-297 (1997); Pilon-Smits et al., "Trehalose-Producing Transgenic Tobacco Plants Show Improved Growth Performance Under Drought Stress," *J. Plant Physiol.*, 152:525-532 (1998)).

The present invention is directed, inter alia, to producing transgenic monocot plants with improved low temperature stress, water stress, and salt stress tolerance.

SUMMARY OF THE INVENTION

The present inventors have earnestly studied to develop a method for increasing the resistance of monocot plants against abiotic stresses. As a result, the inventors have identified that when a fusion gene of trehalose-6-phosphate synthetase (TPS) gene and trehalose-6-phosphate phosphatase (TPP) gene is introduced and expressed in monocot plants, stress resistance of the plants against dehydration, high salt level and low temperature can be enhanced without inhibition of the growth level, and thus, completed the present invention.

Consequently, an object of the present invention is to provide a method for increasing resistance of monocot plants against abiotic stresses by expressing a fusion gene of TPS gene and TPP gene while maintaining phenotypic normalcy.

Another object of the present invention is to provide a method for producing monocot plants having increased resistance against abiotic stresses by expressing a fusion gene of TPS gene and TPP gene.

Another object of the present invention is to provide a method for producing monocot plants without morphological growth defects, such as growth and development disturbance and warped roots, and having increased resistance against abiotic stresses by expressing a fusion gene of the TPS gene and the TPP gene.

Another object of the present invention is to provide a method for producing monocot plants having increased resistance against abiotic stresses by expressing a fusion gene (TPSP) of the TPS gene and the TPP gene and which exhibit normal growth and development characteristics.

The present invention relates to a method for increasing the resistance of monocot plants to better withstand abiotic stress, such as dehydration-stress, salt-stress or cold-stress, which comprises transforming a monocot plant with a recombinant plasmid containing a bifunctional fusion enzyme gene (TPSP) of the trehalose-6-phosphate synthetase (TPS) gene and the trehalose-6-phosphate phosphatase (TPP) gene to express the TPSP gene, thereby limiting the accumulation of trehalose-6-phosphate and enhancing the accumulation of trehalose in the transformed monocot plants to while maintaining normal growth characteristics.

Preferably, the TPS gene and TPP gene are derived from *E. coli* or yeast. The method according to the present invention can be used to increase the resistance of monocot plants, especially in the rice, wheat, barley and maize monocot plants, which are commercially important plants.

In one aspect of the present invention, introduction of the expressible bifunctional fusion gene into a recipient plant cell, i.e., transformation, is carried out according to *Agrobacterium*-mediated method.

The present invention also relates to a transgenic monocot plant transformed with a nucleic acid encoding an enzyme for trehalose biosynthesis, under the control of an inducible promoter, that confers low temperature, salt, and water stress tolerance to a monocot plant.

The present invention further relates to a monocot plant cell or protoplast transformed with a nucleic acid encoding an enzyme for trehalose biosynthesis, under control of an inducible promoter, that confers low temperature, salt, and water stress tolerance to a monocot plant regenerated from a monocot plant cell or protoplast.

The present invention also relates to a method of conferring tolerance to low temperature, salt, and water stress to a monocot plant by transforming a monocot plant cell or protoplast with a nucleic acid encoding an enzyme for trehalose biosynthesis, under control of an inducible promoter, under conditions effective to impart low temperature, salt, and water stress tolerance to monocot plants regenerated from the monocot plant cell or protoplast.

Another aspect of the present invention further relates to a method of increasing tolerance of monocot plant to low temperature, salt, or water stress conditions by increasing the levels of an enzyme for trehalose biosynthesis in the monocot plant.

The present invention also relates to a transgenic monocot plant transformed with a plasmid that confers low temperature, salt, and water stress tolerance to the monocot plant where the plasmid comprises a first nucleic acid encoding trehalose-6-phosphate synthase, a first inducible promoter, the promoter located 5' to the first nucleic acid and controlling expression of the first nucleic acid, and a first termination sequence located 3' to the first nucleic acid.

Considering the importance of rice as a major crop, developing new cultivars with enhanced abiotic stress tolerance would undoubtedly have an enormous impact on global food production. It was decided to improve abiotic stress tolerance by transforming rice with a trehalose-6-phosphate synthase/phosphatase (TPSP) fusion gene that includes the coding regions of the *E. coli* otsA and otsB genes (encoding TPS and TPP, respectively) (Seo et al., "Characterization of a Bifunctional Enzyme Fusion of Trehalose-6-Phosphate Synthetase and Trehalose-6-Phosphate Phosphatase of *Escherichia coli*," *Appl. Environ. Microbiol.*, 66:2484-2490 (2000), which is hereby incorporated by reference in its entirety). This approach has the dual advantages of necessitating only a single transformation event and producing a higher net catalytic efficiency for trehalose formation (Seo et al., "Characterization of a Bifunctional Enzyme Fusion of Trehalose-6-Phosphate Synthetase and Trehalose-6-Phosphate Phosphatase of *Escherichia coli*," *Appl. Environ. Microbiol.*, 66:2484-2490 (2000), which is hereby incorporated by reference in its entirety). Because *Indica* rice varieties represent 80% of rice grown worldwide, the economically valuable *Indica* rice Pusa Basmati-1 (PB-1) was chosen to transform, even though transformation and regeneration are more difficult than in *Japonica* rice varieties. Therefore, whatever has been accomplished with an *Indica* rice works equally well with a *Japonica* rice variety.

It was shown that engineering trehalose overproduction in rice can be achieved by stress-inducible or tissue-specific expression of bifunctional TPSP fusion enzyme without any detrimental effect on plant growth or grain yield. During abiotic stress, transgenic plants accumulated increased amounts of trehalose and showed high levels of tolerance to salt, drought, and low-temperature stresses, as compared with the nontransformed plant. These results demonstrate the potential use of the transgenic approach in developing new rice cultivars with increased abiotic stress tolerance and enhanced rice productivity.

The present invention allows the production of monocot plants with increased tolerance to low temperature stress, salt stress and water stress (drought). In particular, increased tolerance in response to low temperature, salt, and water stress can be achieved by the activation of trehalose biosynthesis under the control of an inducible promoter.

BRIEF DESCRIPTION OF THE DRAWINGS

FIGS. 5A-E show a schematic representation of the expression vectors and DNA-blot hybridization analysis. Two binary plasmids, each containing the trehalose biosynthetic fusion gene (TPSP) that includes the coding regions of the *E. coli* otsA and otsB genes (encoding TPS and TPP, respectively), were constructed and transformed into *Indica* rice. FIG. 5A shows the pSB 109-TPSP plasmid. FIG. 5B shows the pSB-RTSP plasmid. Shaded boxes represent promoter elements (ABA, ABA-inducible; rbcS, rice rbcS; 35S, cauliflower mosaic virus 35S promoter); RB and LB represent T-DNA border on the right and left sides, respectively. FIG. 5C shows a more detailed schematic representation of pSB109-TPSP and pSB-RTSP including several restriction endonucleotide sites. FIG. 5 shows a DNA-blot hybridization analysis from nontransformed control (NTC) plant, and representative transgenic plants of nine A-lines (FIG. 5D) and five R-lines (FIG. 5E) that were transformed with the plasmid pSB109-TPSP and pSB-RTSP, respectively. The rice genomic DNA was digested with HindIII (a unique site in the plasmid pSB109-TPSP, whereas two sites are present in the plasmid pSB-RTSP) and DNA blot hybridization analysis was performed with the 2.2-kb TPSP fusion gene as the probe. Molecular sizes (kb) are indicated.

FIG. 6A shows plant roots after 4 weeks of continuous 100 mM NaCl stress; the plants were not stressed in NTC. FIG. 6B shows dry weight of shoots (black bars) and roots (white bars) of plants grown under salt stress (NTS, R80, and A05) or no stress (NTC) conditions. FIG. 6C shows Western blots of leaf extracts (20 µg of proteins) immediately after salt stress of plants. (FIGS. 6D-F) Plant mineral nutrient content in shoots (black bars) and roots (white bars) under salt stress (NTS, R80, and A05) or no stress (NTC) conditions. FIG. 6D shows $Na^+$. FIG. 6E shows $K^+$. FIG. 6 F shows $Na^+/K^+$ ratio. The ionic concentration is presented as mg/g dry weight. Values are the means±SD (n=5).

FIG. 7A shows plants grown under well watered conditions (NTC, nontransgenic plants). FIG. 7B shows plants of the same age after two cycles of drought-stress treatment (NTS, nontransgenic plants after drought stress). FIGS. 7C and D show chlorophyll fluorescence measurements on young, fully expanded leaves during the first cycle of 100 h of continuous drought stress. FIG. 7C shows $\phi_{PSII}$, a measure of the efficiency of PS II photochemistry under ambient growth conditions. FIG. 7D shows decreases in Fv/Fm are a measure of photooxidative damage to PS II. ▲, nontransformed plants; ■, R80; ●, A05. Dotted lines represent the range of values for nonstressed control plants of all lines. Data represent means±SD (n=5) from independent plants.

In FIG. 10A, the chromatogram shows the PAD-response profile from a leaf tissue extract of transgenic line A05.

FIG. 11 B shows $\phi_{PSII}$.

DETAILED DESCRIPTION OF THE INVENTION

Figure 1:
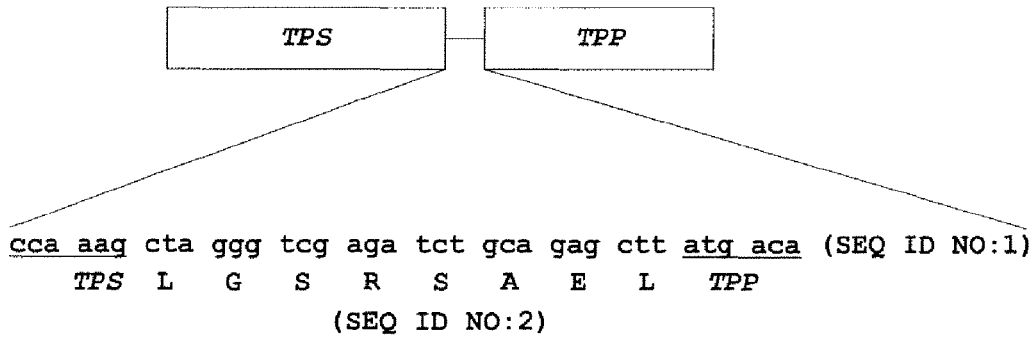
FIG. 1 is a drawing showing the map of TPSP gene as the fused recombinant gene of TPS and TPP.

According to one aspect of the present invention, the method for increasing resistance of monocot plants against abiotic stresses comprises a step of transforming monocot plants with a recombinant plasmid containing a fused gene (TPSP) of trehalose-6-phosphate synthetase (TPS) gene and trehalose-6-phosphate phosphatase (TPP) gene to express TPSP gene. In this method, the TPS gene and TPP gene are derived from *E. coli* or yeast and introduced into monocot plants such as rice, barley, wheat or maize by means of the *Agrobacterium*-mediated method. Although the abiotic stresses in this method are not particularly restricted, they can include dehydration-stress, salt-stress or cold-stress.

The method for producing monocot plants having increased resistance against abiotic stresses according to the present invention is conducted through the same steps as the method for increasing stress of monocot plants against said abiotic stresses, except that the recombinant plasmid containing TPSP gene is introduced into monocot plants or their ancestor cells as long as the cells are capable of being regenerated into plants.

Hereinafter, the present invention will be more specifically explained.

Up to the present, attempts to increase stress resistance in plants using trehalose has been done in only dicotyledon plants due to difficulties including the absence of suitable vectors for monocot plants and a deficiency of research papers. However, although the expression of trehalose increases the stress resistance in dicotyledon plants, it could not obtain any remarkable effect due to the side effect of severely inhibiting the growth of plants. Thus, such attempt has never been made in monocot plants as well.

In order to increase stress resistance in monocot plants as valuable food resources, the present inventors incorporated a fusion gene of genes coding for trehalose-6-phosphate synthetase (TPS) and trehalose-6-phosphate phosphatase (TPP), both of which are the enzymes required for trehalose synthesis, into a vector containing Ubi1 promoter exhibiting a relatively high activity in monocot plants to construct the recombinant plasmid, which was then introduced into rice plants by means of transformation mediated by *Agrobacterium tumefaciens*.

Then, the transformed rice genotypes were analyzed with Southern Blot to identify that introduced genes were stably integrated into the rice chromosomes. Further, rice RNAs extracted from said rice leaves were analyzed with Northern Blot to identify that the genes introduced were normally expressed. In addition, it has been confirmed through carbohydrate quantitative analysis that trehalose was expressed at as high a level as 200 times the expression level known from tobacco transformed with TPS or TPP in the prior art. The observation at the level of cultivation revealed that contrary to dicotyledon plants, the overexpression of trehalose in rice plants does not greatly affect the growth of rice as monocot plants, and further, it has also been identified that trehalose results in increasing the resistance against abiotic stresses, such as dehydration, salt and low temperature.

Accordingly, it is expected that the method of the present invention can largely contribute to the production and quality improvement of valuable agricultural crops since it can increase the resistance of monocot plants against various stresses.

The present invention also relates to a transgenic monocot plant transformed with a nucleic acid encoding an enzyme for trehalose biosynthesis, under the control of an inducible promoter, that confers low temperature, salt, and water stress tolerance to a monocot plant.

The invention provides a method of producing a monocot plant cell or protoplast useful for regeneration of a low temperature stress, salt stress or water stress tolerant monocot plant by transforming a monocot plant cell or protoplast with a nucleic acid encoding an enzyme for trehalose biosynthesis under the control of an inducible promoter. Once transformation has occurred, the monocot plant cell or protoplast can be regenerated to form a transgenic monocot plant.

The present invention also relates to a method of conferring low temperature, salt, and water stress tolerance to a monocot plant by transforming a monocot plant cell or protoplast with a nucleic acid encoding an enzyme for trehalose biosynthesis, under control of an inducible promoter, under conditions effective to impart low temperature, salt, and water stress tolerance to monocot plants produced from the monocot plant cell or protoplast. This method includes transforming the monocot plant with an expression cassette comprising an inducible promoter and a nucleic acid encoding an enzyme for trehalose biosynthesis that confers low temperature, salt, and water stress tolerance to monocot plants, wherein the inducible promoter and the nucleic acid are operably linked together to permit expression of the nucleic acid. In a preferred embodiment, the inducible promoter is comprised of at least one ABRC unit and a minimal promoter. In another preferred embodiment, the at least one inducible element is a light-inducible rbcS promoter fragment with a chloroplast-targeting transit peptide.

Another aspect of the present invention further relates to a method of increasing tolerance of monocot plant to low temperature, salt, or water stress conditions by increasing the levels of an enzyme for trehalose biosynthesis in the monocot plant.

The present invention also relates to a transgenic monocot plant transformed with a plasmid that confers low temperature, salt, and water stress tolerance to the monocot plant where the plasmid comprises a first nucleic acid encoding trehalose-6-phosphate synthase, a first inducible promoter, the promoter located 5' to the first nucleic acid and controlling expression of the first nucleic acid, and a first termination sequence located 3' to the first nucleic acid.

Monocot plants, which can be transformed in accordance with the subject invention, are members of the family Gramineae (also known as Poaceae), and include rice (genus *Oryza*), wheat, maize (corn), barley, oat, rye, millet, and sorghum. Preferably, the cereal is rice, wheat, or corn, and most preferably the cereal is rice. Many species of cereals can be transformed, and, within each species, there are numerous subspecies and varieties that can be transformed. For example, within the rice species is subspecies *Indica* rice (*Oryza sativa* ssp. *Indica*), which includes the varieties IR36, IR64, IR72, Pokkali, Nona Bokra, KDML105, Suponburi 60, Suponburi 90, Basmati 385, and Pusa Basmati 1. Another rice subspecies is *Japonica*, which includes Nipponbare, Kenfeng, and Tainung 67. Examples of suitable maize varieties include A188, B73, VA22, L6, L9, K1, 509, 5922, 482, HNP, and IGES. Examples of suitable wheat varieties include Pavon, Bob White, Hi-Line, Anza, Chris, Coker 983, FLA301, FLA302, Fremont, and Hunter.

Having identified the plant of interest, plant cells suitable for transformation include mature embryos, immature embryos, calli, suspension cells, and protoplasts. It is particularly preferred to use mature embryos and immature embryos.

In a preferred embodiment, the at least one ABRC unit is from a barley HVA22 gene or a barley HVA1 gene. The sequence for the at least one ABRC unit from a barley HVA22 gene, a 49-bp ABA-responsive complex, is set forth in Shen et al., "Functional Dissection of an Abscisic Acid (ABA)-Inducible Gene Reveals Two Independent ABA-Responsive Complexes Each Containing a G-Box and Novel Acting Element," *The Plant Cell*, 7:295-307 (1995), which is hereby incorporated by reference in its entirety. The sequence for the ABRC unit from a barley HVA1 gene is set forth in Shen et al., "Modular Nature of Abscisic Acid (ABA) Response Complexes: Composite Promoter Units that are Necessary and Sufficient for Induction of Gene Expression in Barley," *The Plant Cell*, 8:1107-1119 (1996). In a most preferred embodiment, up to four of the ABRC units are operably linked together in the expression cassette.

Suitable nucleic acids that increase tolerance to low temperature stress, salt stress, and water stress in monocot plants are genes the regulate the expression of stress-responsive genes and genes that encode enzymes involved in trehalose biosynthesis. Enzymes that encode trehalose biosynthesis can be isolated from a large number of organisms including bacteria, yeast, and invertebrates (see generally, Crowe et al., "Anhydrobiosis," *Annu. Rev. Physiol.*, 54:579-599 (1992), which is hereby incorporated by reference in its entirety). In a preferred embodiment, a nucleic acid that encodes an enzyme involved in trehalose biosynthesis is a DNA encoding trehalose-6-phosphate synthase. Preferably, the TPS1 gene from yeast encodes the trehalose-6-phosphate synthase (for comparison of different yeast TPS1 genes, see Kwon et al., "Cloning and Characterization of Genes Encoding Trehalose-6-phosphate Synthase (TPS1) and Trehalose-6-phosphate Phosphatase (TPS2) from *Zygosaccharomyces rouxii*," *FEMS Yeast Res.*, 3:433-440 (2003), which is hereby incorporated by reference in its entirety). More preferably, the otsA gene from *Escherichia coli* encodes the trehalose-6-phosphate synthase. In another preferred embodiment, a nucleic acid that encodes an enzyme involved in trehalose biosynthesis is a DNA encoding trehalose-6-phosphate phosphatase. Preferably, the TPS2 gene from yeast encodes the trehalose-6-phosphate phosphatase (for comparison of different yeast TPS2 genes, see Kwon et al., "Cloning and Characterization of Genes Encoding Trehalose-6-phosphate Synthase (TPS1) and Trehalose-6-phosphate Phosphatase (TPS2) from *Zygosaccharomyces rouxii*," *FEMS Yeast Res.*, 3:433-440 (2003), which is hereby incorporated by reference in its entirety). More preferably, the otsB gene from *Escherichia coli* encodes the trehalose-6-phosphate phosphatase. In a more preferred embodiment, both the trehalose-6-phosphate synthase (otsA) and trehalose-6-phosphate phosphatase (otsB) are coexpressed in the monocot plant. In a most preferred embodiment, the trehalose-6-phosphate synthase (otsA) and trehalose-6-phosphate phosphatase (otsB) are expressed as a fusion protein in the monocot plant. The sequence of the otsA and otsB genes can be found in Kaasen et al., "Analysis of the otsBA Operon for Osmoregulatory Trehalose Synthesis in *Escherichia coli* and Homology of the OtsA and OtsB Proteins to the Yeast Trehalose-6-phosphate synthase/phosphatase complex," *Gene*, 145:9-15 (1994), which is hereby incorporated by reference in its entirety.

Suitable minimal promoters include Act1 of rice, rbcS of rice, a shortened α-amylase promoter of barley or rice, a shortened maize ubiquitin promoter, or a shortened CaMV 35S promoter.

In a preferred embodiment, the minimal promoter is an inducible promoter.

In a more preferred embodiment, the minimal promoter is the light inducible promoter rbcS of rice.

Most preferably, the minimal promoter is the stress inducible minimal Act1 promoter of rice and the sequence can be found in Su et al, "Dehydration Stress-regulate Transgene Expression in Stably Transformed Rice Plants," *Plant Physiol.*, 117:913-922 (1998), which is hereby incorporated by reference in its entirety.

In a preferred embodiment, the expression cassette comprising the inducible promoter and the nucleic acid encoding an enzyme for trehalose biosynthesis increases tolerance to low temperature stress, salt stress, and water stress in monocot plants.

These monocot plant cells are transformed with a nucleic acid, which could be RNA or DNA and which is preferably cDNA, encoding a molecule that increases tolerance to low temperature stress, salt stress, and water stress in monocot plants. The nucleic acid can be biologically isolated or synthetic and encodes for an enzyme for trehalose biosynthesis. In the following Examples, a key enzyme for biosynthesis, trehalose-6-phosphate synthase (TPS), is encoded by the otsA gene of *E. coli*. In the following Examples, a second key enzyme for biosynthesis, trehalose-6-phosphate phosphatase (TPP), is encoded by the otsB gene of *E. coli*.

Transformation of plant cells can be accomplished by using a plasmid. The plasmid is used to introduce the nucleic acid that increases tolerance to salt stress and drought stress in plants into the plant cell. Accordingly, a plasmid preferably includes a DNA molecule that increases tolerance to salt stress and drought stress in plants inserted into a unique restriction endonuclease cleavage site. Heterologous DNA, as used herein, refers to DNA not normally present in the particular host cell transformed by the plasmid. DNA is inserted into the vector using standard cloning procedures readily known in the art. This generally involves the use of restriction enzymes and DNA ligases, as described by Sambrook et al., *Molecular Cloning: A Laboratory Manual*, 2d edition, Cold Spring Harbor Laboratory Press, Cold Spring Harbor, N.Y., which is hereby incorporated by reference in its entirety. The resulting plasmid, which includes a nucleic acid that, increases tolerance to salt stress and drought stress in plants can then be used to transform a host cell, such as an *Agrobacterium* and/or a plant cell. (See generally, *Plant Molecular Biology Manual*, 2d Edition, Gelvin et al., Eds., Kluwer Academic Press, Dordrecht, Netherlands (1994), which is hereby incorporated by reference in its entirety).

For plant transformation, the plasmid preferably also includes a selectable marker for plant transformation. Commonly used plant selectable markers include the hygromycin phosphotransferase (hpt) gene, the phosphinothricin acetyl transferase gene (bar), the 5-enolpyruvylshikimate-3-phosphatesynthase gene (EPSPS), neomycin 3'-O-phosphotransferase gene (npt II), or acetolactate synthase gene (ALS). Information on these selectable markers can be found in "Markers for Plant Gene Transfer" in *Transgenic Plants*, Kung et al., Eds., Vol. 1, pp. 89-123, Academic Press, NY (1993), which is hereby incorporated by reference in its entirety. In a preferred embodiment, the plasmid includes the phosphinothricin acetyl transferase gene (bar) in a selection cassette as a selectable marker for plant transformation under control of the cauliflower mosaic virus 35S promoter.

In a preferred embodiment, the plasmid is designated pSB109-TPSP or pSB-RTSP, each of which includes an otsA and otsB fusion gene.

For plant transformation, the plasmid also preferably includes a nucleic acid molecule encoding a 3' terminator such as that from the 3' non-coding region of genes encoding a proteinase inhibitor, actin 1, or nopaline synthase (nos). In a preferred embodiment, the plasmid includes a nucleic acid molecule encoding the 3' non-coding region of the proteinase inhibitor II gene (pinII) as a 3' terminator for the expression cassette comprising the inducible promoter and the nucleic acid encoding an enzyme for trehalose biosynthesis. Preferably, the plasmid includes a nucleic acid molecule encoding 3' non-coding region of the nopaline synthase gene (nos) as a 3' terminator for the selection cassette for plant transformation.

Other suitable plasmids for use in the subject invention can be constructed. For example, genes encoding a nucleic acid that increases trehalose biosynthesis and that increases tolerance to low temperature stress, salt stress, and water stress in monocot plants other than the otsA gene or the otsB gene of *E. coli* could be ligated into the parent plasmid SB109-TPSP or SB-RTSP after use of restriction enzymes to remove the otsA gene, the otsB gene, or the otsA/otsB fusion gene. Other minimal promoters could replace the rice actin 1 gene promoter present in plasmid SB109-TPSP or the rbcS gene promoter in plasmid SB-RTSP. Alternatively, other plasmids in general containing genes encoding a nucleic acid that increases trehalose biosynthesis and that increases tolerance to low temperature stress, salt stress, and water stress in monocot plants under the control of a suitable minimal promoter, with suitable selectable markers, can be readily constructed using techniques well known in the art.

Having identified the plasmid, one technique of transforming monocot plant cells with a nucleic acid that increases tolerance to low temperature stress, salt stress, and water stress in plants is by contacting the plant cell with an inoculum of an *Agrobacterium* bacteria transformed with the plasmid comprising the nucleic acid that increases tolerance to low temperature stress, salt stress, and water stress in monocot plants. Generally, this procedure involves inoculating the plant cells with a suspension of the transformed bacteria and incubating the cells for 48 to 72 hours on regeneration medium without antibiotics at 25-28° C.

Bacteria from the genus *Agrobacterium* can be utilized to transform plant cells. Suitable species include *Agrobacterium tumefaciens* and *Agrobacterium rhizogenes*. *Agrobacterium tumefaciens* (e.g., strains LBA4404 or EHA105) is particularly useful due to its well-known ability to transform plants.

In inoculating the cells of plants with *Agrobacterium* according to the subject invention, the bacteria must be transformed with a vector, which includes a gene encoding for an enzyme for trehalose biosynthesis.

Plasmids, suitable for incorporation in *Agrobacterium*, which include a nucleic acid that increases tolerance to low temperature stress, salt stress, and water stress in plants, contain an origin of replication for replication in the bacterium *Escherichia coli*, an origin of replication for replication in the bacterium *Agrobacterium tumefaciens*, T-DNA right border sequences for transfer of genes to plants, and marker genes for selection of transformed plant cells. Particularly preferred is the vector pBI121, which contains a low-copy RK2 origin of replication, the neomycin phosphotransferase (nptII) marker gene with a nopaline synthase (NOS) promoter and a NOS 3' polyadenylation signal. T-DNA plasmid vector pBI121 is available from Clontech Laboratories, 4030 Fabian Way, Palo Alto, Calif. 94303. A nucleic acid that increases tolerance to low temperature stress, salt stress, and water stress in monocot plants is inserted into the vector to replace the beta-glucuronidase (GUS) gene.

Typically, *Agrobacterium* spp. are transformed with a plasmid by direct uptake of plasmid DNA after chemical and heat treatment, as described by Holsters et al., "Transfection and Transformation of *Agrobacterium tumefaciens*," *Mol. Gen. Genet.*, 163:181-187 (1978), which is hereby incorporated by reference in its entirety; by direct uptake of DNA after electroporation, as described by Shen et al., "Efficient Transformation of *Agrobacterium* spp. by High Voltage Electroporation," *Nucleic Acids Research*, 17: 8385 (1989), which is hereby incorporated by reference in its entirety; by triparental conjugational transfer of plasmids from *Escherichia coli* to *Agrobacterium* mediated by a Tra+ help strain as described by Ditta et al., "Broad Host Range DNA Cloning System for Gram-negative Bacteria: Construction of a Gene Bank of *Rhizobium meliloti*," *Proc. Natl. Acad. Sci. USA*, 77:7347-7351 (1981), which is hereby incorporated by reference in its entirety; or by direct conjugational transfer from *Escherichia coli* to *Agrobacterium* as described by Simon et al., "A Broad Host Range Mobilization System for in vivo Genetic Engineering: Transposon Mutagenesis in Gram-Negative Bacteria," *Biotechnology*, 1:784-791 (1982), which is hereby incorporated by reference in its entirety.

Another method for introduction of a containing nucleic acid encoding an enzyme for trehalose biosynthesis into a plant cell is by transformation of the plant cell nucleus, such as by particle bombardment. As used throughout this application, particle bombardment (also known as biolistic transformation) of the host cell can be accomplished in one of several-ways. The first involves propelling inert or biologically active particles at cells. This technique is disclosed in U.S. Pat. Nos. 4,945,050, 5,036,006, and 5,100,792, all to Sanford et al., which are hereby incorporated by reference in their entirety. Generally, this procedure involves propelling inert or biologically active particles at the cells under conditions effective to penetrate the outer surface of the cell and to be incorporated within the interior thereof. When inert particles are utilized, the plasmid can be introduced into the cell by coating the particles with the plasmid containing the heterologous DNA. Alternatively, the target cell can be surrounded by the plasmid so that the plasmid is carried into the cell by the wake of the particle. Biologically active particles (e.g., dried bacterial cells containing the plasmid and heterologous DNA) can also be propelled into plant cells.

A further method for introduction of the plasmid into a plant cell is by transformation of plant cell protoplasts (stable or transient). Plant protoplasts are enclosed only by a plasma membrane and will therefore take up macromolecules like heterologous DNA. These engineered protoplasts can be capable of regenerating whole plants. Suitable methods for introducing heterologous DNA into plant cell protoplasts include electroporation and polyethylene glycol (PEG) transformation. As used throughout this application, electroporation is a transformation method in which, generally, a high concentration of DNA (containing heterologous DNA) is added to a suspension of host cell protoplasts and the mixture shocked with an electrical field of 200 to 600 V/cm. Following electroporation, transformed cells are identified by growth on appropriate medium containing a selective agent.

As used throughout this application, transformation encompasses stable transformation in which the plasmid is integrated into the plant chromosomes.

In the Examples which follow, rice has been transformed using the *Agrobacterium* method as described in Hiei et al., "Efficient Transformation of Rice (*Oryza sativa* L.) Mediated by *Agrobacterium* and Sequence Analysis of the Boundaries of the T-DNA," *The Plant Journal*, 6:271-282 (1994), which is hereby incorporated by reference in its entirety, biolistic transformation. Other methods of transformation have also been used to successfully transform rice plants, including the protoplast method (for a review, see Cao et al., "Regeneration of Herbicide Resistant Transgenic Rice Plants Following Microprojectile-Mediated Transformation of Suspension Culture Cells," *Plant Cell Rep.*, 11:586-591 (1992), which is hereby incorporated by reference in its entirety), and the biolistic transformation method (disclosed in U.S. Pat. Nos. 4,945,050, 5,036,006, and 5,100,792, all to Sanford et al., which are hereby incorporated by reference in their entirety). Biolistic transformation has been used successfully to transform wheat (for a review, see Weeks et al., "Rapid Production of Multiple Independent Lines of Fertile Transgenic Wheat (*Triticum aestivum*)," *Plant Physiol.*, 102:1077-1084 (1993), which is hereby incorporated by reference in its entirety). Biolistic transformation has also been used to successfully transform maize (for a review, see Mackey et al., "Transgenic Maize," In *Transgenic Plants*, Kung et al., Eds., vol. 2, pp. 21-33 (1993), which is hereby incorporated by reference in its entirety) and wheat (see U.S. Pat. No. 5,405,765 to Vasil et al., which is hereby incorporated by reference in its entirety).

Once a monocot plant cell or protoplast is transformed in accordance with the present invention, it is regenerated to form a transgenic monocot plant. Generally, regeneration is accomplished by culturing transformed cells or protoplasts on medium containing the appropriate growth regulators and nutrients to allow for the initiation of shoot meristems. Appropriate antibiotics are added to the regeneration medium to inhibit the growth of *Agrobacterium* or other contaminants and to select for the development of transformed cells or protoplasts. Following shoot initiation, shoots are allowed to develop in tissue culture and are screened for marker gene activity.

In suitable transformation methods, the monocot plant cell to be transformed can be in vitro or in vivo, i.e. the monocot plant cell can be located in a monocot plant.

The present invention also relates to a transgenic monocot plant transformed with a nucleic acid that increases tolerance to low temperature stress, salt stress, and water stress operably linked to an inducible promoter.

The invention also provides seed produced by the transgenic monocot plant. The invention is also directed to seed, which upon germination, produces the transgenic monocot plant.

Also encompassed by the present invention are transgenic monocot plants transformed with fragments of the nucleic acids that increase tolerance to low temperature stress, salt stress, and water stress of the present invention. Suitable fragments capable of conferring low temperature stress, salt stress or water stress tolerance to monocot plants can be constructed by using appropriate restriction sites. A fragment refers to a continuous portion of the nucleic acid that increases tolerance to salt stress and drought stress that is less than the entire molecule.

Non-essential nucleotides could be placed at the 5' and/or 3' ends of the fragments (or the full length nucleic acids that increase tolerance to salt stress and drought stress) without affecting the functional properties of the fragment or molecule (i.e. in increasing water stress or salt stress tolerance). For example, the nucleic acid that increases tolerance to low temperature stress, salt stress, and water stress may be conjugated to a signal (or leader) sequence at the N-terminal end (for example) of the nucleic acid that increases tolerance to low temperature stress, salt stress, and water stress which co-translationally or post-translationally directs transfer of the nucleic acid that increases tolerance to low temperature stress, salt stress, and water stress. The nucleotide sequence may also be altered so that the nucleic acid that increases tolerance to low temperature stress, salt stress, and water stress is conjugated to a linker or other sequence for ease of synthesis, purification, or identification.

The transgenic cereal plant cell or protoplast or plant can also be transformed with a nucleic acid encoding a selectable marker, such as the bar gene, to allow for detection of transformants, and with a nucleic acid encoding the cauliflower mosaic virus 35S promoter to control expression of the bar gene. Other selectable markers include genes encoding EPSPS, nptII, or ALS. Other promoters include those from genes encoding actin 1, rbcS, ubiquitin, and PINII. These additional nucleic acid sequences can also be provided by the plasmid encoding a gene that imparts tolerance to low temperature stress, salt stress, and water stress and its promoter. Where appropriate, the various nucleic acids could also be provided by transformation with multiple plasmids.

While the nucleic acid that increases tolerance to low temperature stress, salt stress, and water stress referred to herein encodes, for example, a gene that imparts tolerance to low temperature stress, salt stress, and water stress, nucleotide identity to previously sequenced to low temperature stress, salt stress, and water stress genes is not required. As should be readily apparent to those skilled in the art, various nucleotide substitutions are possible which are silent mutations (i.e. the amino acid encoded by the particular codon does not change). It is also possible to substitute a nucleotide which alters the amino acid encoded by a particular codon, where the amino acid substituted is a conservative substitution (i.e. amino acid "homology" is conserved). It is also possible to have minor nucleotide and/or amino acid additions, deletions, and/or substitutions in the low temperature stress, salt stress, and water stress gene nucleotide and/or amino acid sequences which have minimal influence on the properties, secondary structure, and hydrophilic/hydrophobic nature of the encoded low temperature stress, salt stress, and water stress gene. These variants are encompassed by the present invention.

EXAMPLES

Hereinafter, the present invention will be more specifically illustrated through the following examples. A person having an ordinary knowledge in the relevant technical field will understand that these examples are intended only to specifically explain the present invention and the scope of the present invention is not limited by these examples.

Example 1

Construction of Plasmid and Transformation of Rice Plants

Figure 2:
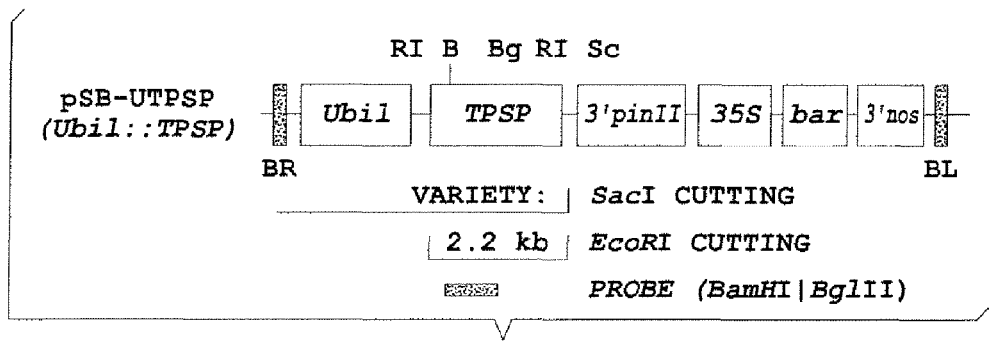
FIG. 2 is a drawing showing the gene map of recombinant plasmid pSB-UTPSP.

The stop codon of *E. coli* TPS gene was removed through PCR and then ligated with TPP gene to construct TPSP as the fusion recombinant gene of TPS and TPP. (See, FIG. 1 and Seo H S et al., *Appl, Environ. Microbiol.*, 66:2484-2490, (2000), which is incorporated by reference as if fully described herein.) The resulting TPSP was linked to maize ubiquitin promoter to construct Ubi1::TPSP, which was inserted into the expression vector containing 35S promoter and bar coding region (phosphinothricin acetyltransferase gene) to construct recombinant plasmid pSB-UTPSP (see, FIG. 2). FIG. 2 is the diagram showing the gene map of recombinant plasmid pSB-UTPSP, wherein BR represents a right-border sequence; BL represents a left-border sequence; 3' pinII represents the 3'-region of potato protease inhibitor II gene; 35S represents 35S promoter, and 3' nos represents the 3'-region of nopaline synthase gene. Since phosphinothricin acetyl transferase encoded into bar gene functions to detoxify the toxicity of phosphinothricin-derived herbicides, it can act as a selective marker. The pSB-UTPSP was introduced into *Agrobacterium tumefaciens* LBA4404 by triparental mating.

For transformation of rice plants with said *Agrobacterium tumefaciens* LBA4404, 70% (v/v) ethanol was added to about 200 unhulled seeds (*Oryza sativa* L. cv Nakdong) and gently mixed together for one minute to sterilize the seeds. Then, ethanol was discarded and the seeds were further sterilized by gentle mixing with 100 ml of 20% (v/v) Clorox for one hour, and then washed several times with sterilized water. Callus induction from the seeds, co-cultivation of callus with *Agrobacterium* containing the plasmid constructed as described above, and the selection of transformed callus were carried out as previously described (see, Jang, I-C. et al., *Mol. Breeding*, 5:453-461, 1999). Rice plants transformed with *Agrobacterium*-mediated method were cultivated in a greenhouse to select only the plants having resistance against the herbicide Basta. According to Southern blot analysis of transgenic rice plants transformed and selected as described above, it could be identified that the introduced transgene was integrated into rice chromosomes and had one to three copy numbers. For further tests, the plants containing a single copy of TPSP gene were selected, and Northern blot analysis using total RNA samples from leaves of the selected plants could observe mRNA of approximately 2.4 kb, thereby it was identified that TPSP was normally expressed.

Example 2

Investigation of Accumulation level of Trehalose in Transgenic Plants

Figure 3A:
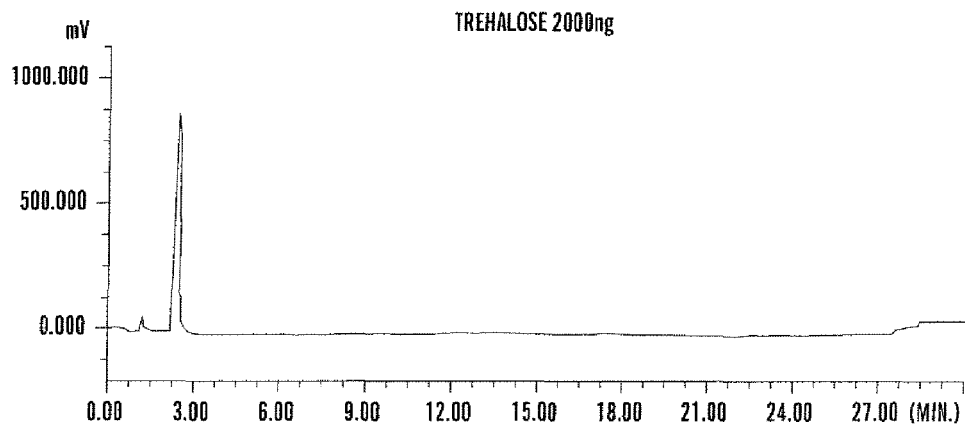
FIG. 3A is the standard HPIC chromatogram of trehalose.

To investigate the accumulation level of trehalose in transgenic plants and the effect of trehalose on the carbohydrate content in plants, leaves and seeds of Ubi1::TPSP as the transgenic rice plants produced in Example I were digested in liquid nitrogen and then extracted with 10 ml/g of water at 100° C. for 10 minutes. The extract was centrifuged, and the resulting supernatant was filtered through a 0.45 Ñ m filter. Then, the quantitative analysis of carbohydrate was carried out by means of DX500 HPIC (high performance ion chromatography, Dionex 500, Dionex, USA) equipped with a 4×250 nm Carbo Pak PA1 column. HPIC was carried out under a linear gradient condition using 150 mM NaOH solution containing 0 mM to 250 mM sodium acetate for 30 minutes. The HPIC result was monitored with ED40 electrochemical detector (Dionex DC Amperometry, Dionex, USA) using commercially available trehalose (Sigma Chemicals Co., USA) as the standard (see, FIG. 3*a*).

Figure 3B:
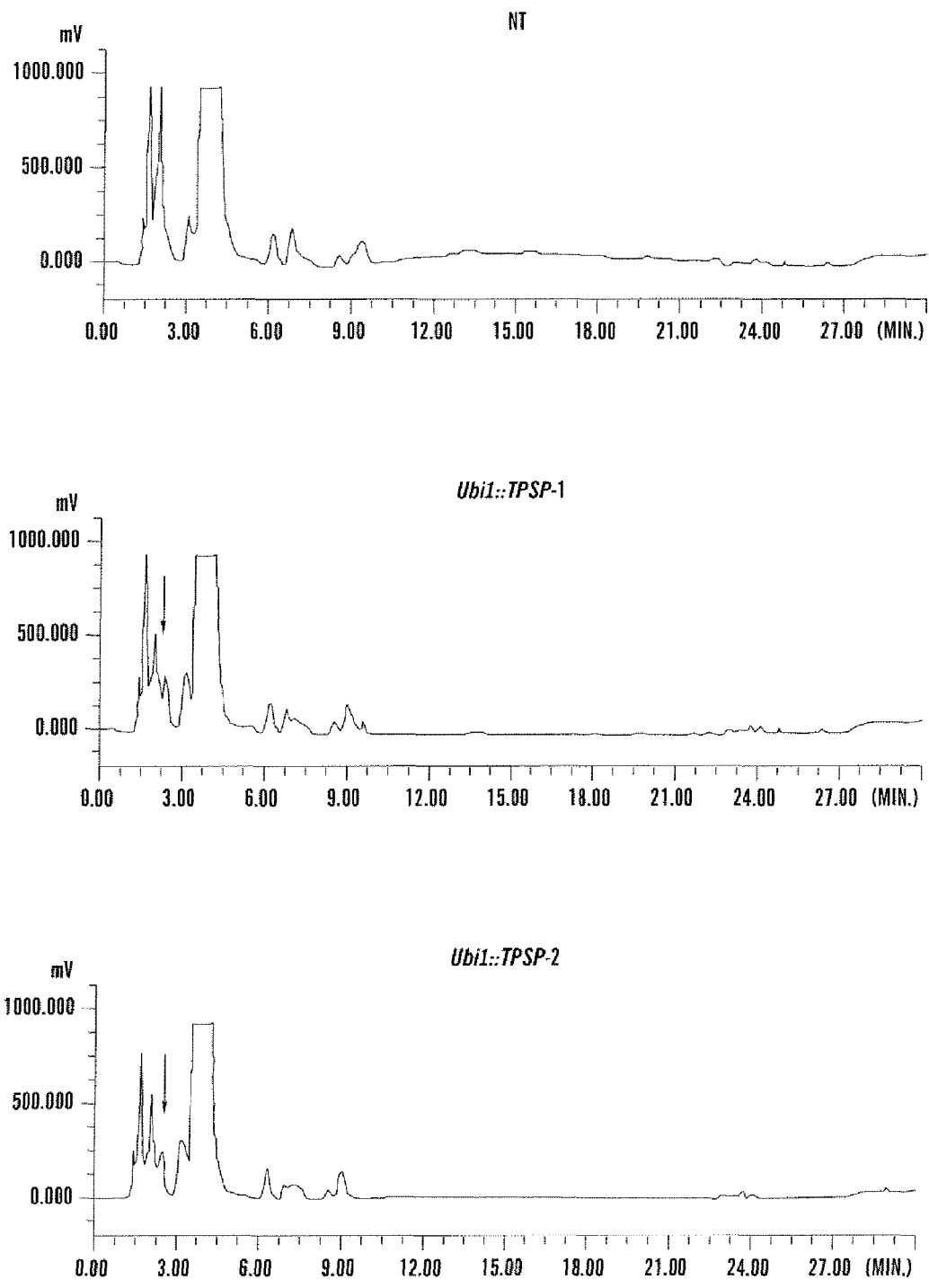
FIG. 3B is HPIC chromatogram showing a carbohydrate profile of Ubi1::TPSP plant leaves.
Figure 3C:
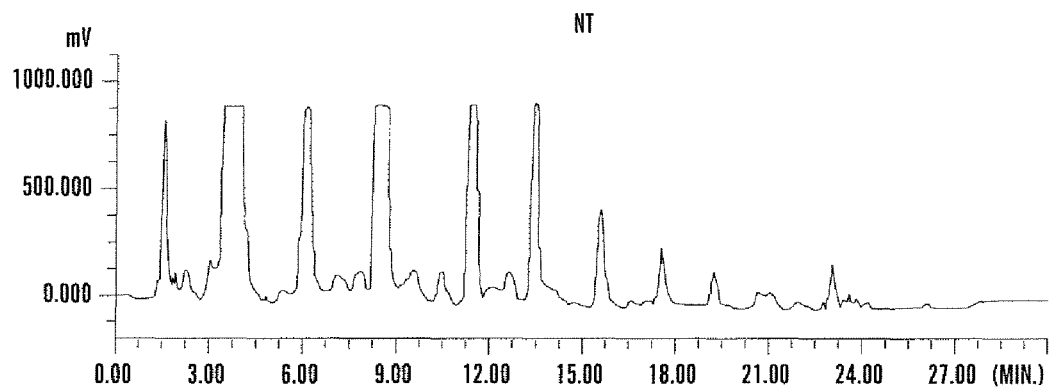
FIG. 3C is HPIC chromatogram showing a carbohydrate profile of the extract of Ubi1::TPSP plant seeds.
Figure 3C:
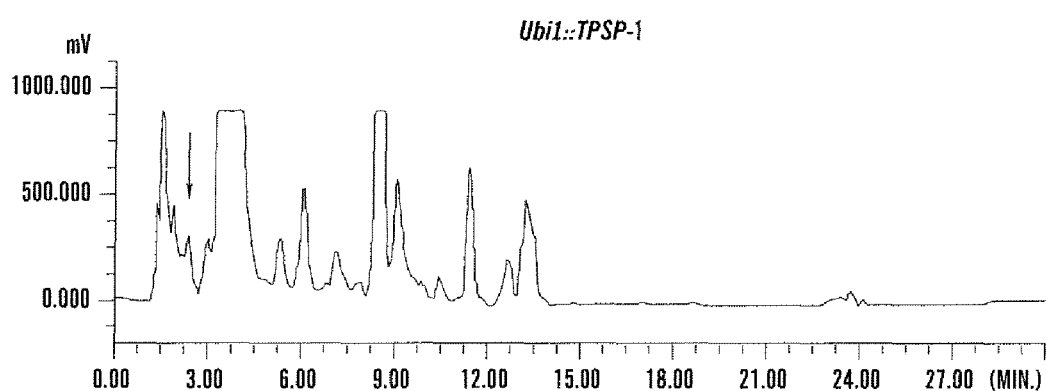
Figure 3C:
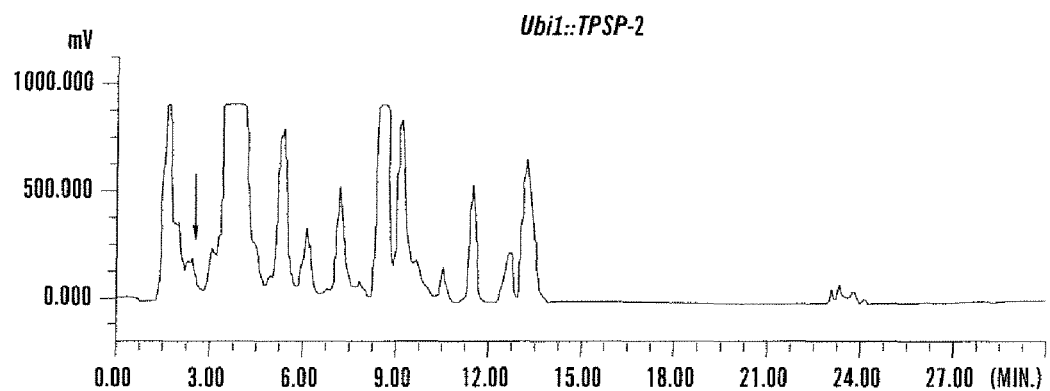

The effects of trehalose on the composition and distribution of respective carbohydrates are shown in FIGS. 3*b* and 3*c*. FIGS. 3*b* and 3*c* are HPIC chromatograms showing carbohydrate profiles in the extracts of Ubi1::TPSP plant leaves and seeds, respectively, wherein NT represents untransformed rice plant, Ubi1::TPSP-1 and Ubi1::TPSP-2 represent two plants containing a single copy number of TPSP gene as selected in Example 1. As can be seen from FIGS. 3*b* and 3*c*, trehalose was present in the leaf and seed extracts of Ubi1::TPSP rice plants at the level of about 1.076 mg/g, which is 200-fold higher than the level known from transgenic tobacco plants transformed with TPS or TPP genes. Further, it could also be identified that the carbohydrate content was substantially not altered in the leaf extract of Ubi1::TPSP rice plants but was greatly altered in the seed extract.

In addition, as the result of observation for the cultivation level of Ubi1::TPSP rice plants, it could be identified that Ubi1::TPSP rice plants grew up to a level similar to untransformed rice plants. Up to the present, transgenic plants transformed with TPS and/or TPP of *E. coli* or yeasts have been known for dicotyledon plants, and it has been reported in these transgenic plants that although trehalose is expressed at a very low level, there occurred such phenomena as severe disturbance of growth and development and warped roots. However, Ubi1::TPSP rice plants did not show any change in root appearance as well as in their growth even though they excessively produced trehalose at the level of 0.1% of the plant mass. Accordingly, it could be found that contrary to dicotyledon plants the overexpression of trehalose in rice plants does not inhibit the normal growth of plants.

Example 3

Increase of Stress-Resistance by Trehalose

The seeds, sterilized with ethanol and Clorox and washed as described in Example 1, were germinated on soil in a growth chamber at 28° C. with cycles of 16 hours light/8 hours dark conditions and then grown for 14 days to produce the young seedlings. For the dehydration-stress treatment, whole plants were air-dried for one hour at 28° C. under light condition of 150 Ñ m/m2/s. For the salt-stress treatment, said young seedlings were grown in a nutrient solution of 0.1% (v/v) Hyponex (Hyponex, Japan) for 2 days, transferred to a fresh nutrient solution containing 9% (w/v) NaCl and then grown under light condition of 150 Ñ m/m2/s for 2 hours at 28° C. For the cold-stress treatment, said young seedlings were grown under light conditions of 150 Ñ m/m2/s for 6 hours at 4° C. Then, the untransformed control group and the transgenic test groups with stress treatment under various conditions were kept for 2 hours under dark condition and their chlorophyll fluorescent levels were measured using a pulse modulation (PAM) fluorometer. The chlorophyll fluorescent level was represented by the ratio (Fv/Fm) of measured minimum fluorescence (Fv) to maximum fluorescence (Fm), wherein the Fv/Fm ratio means the activity of photosystem II, and therefore, can be used as a measure to assess the functional damage of the plants (see, FIGS. 4*a*, 4*b* and 4*c*).

Figure 4A:
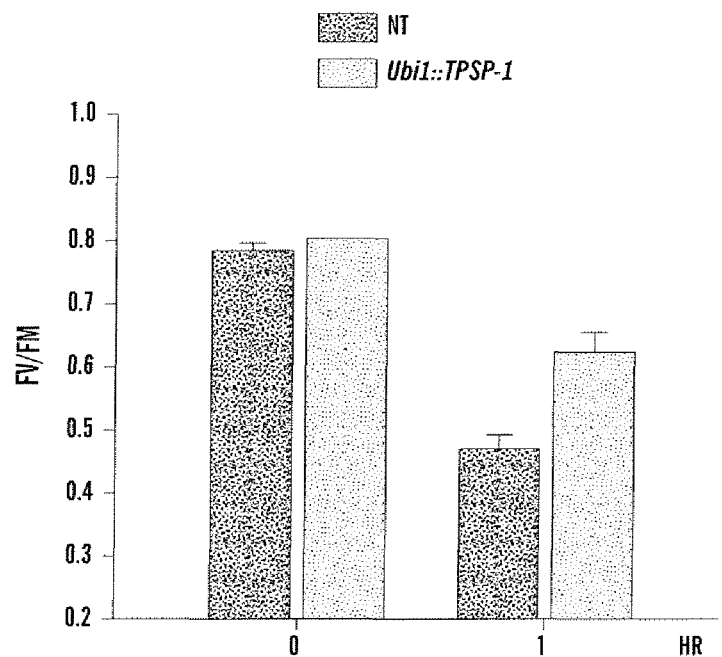
FIG. 4A is a graph showing chlorophyll fluorescence in dehydration-stress treated Ubi1::TPSP rice plants.
Figure 4B:
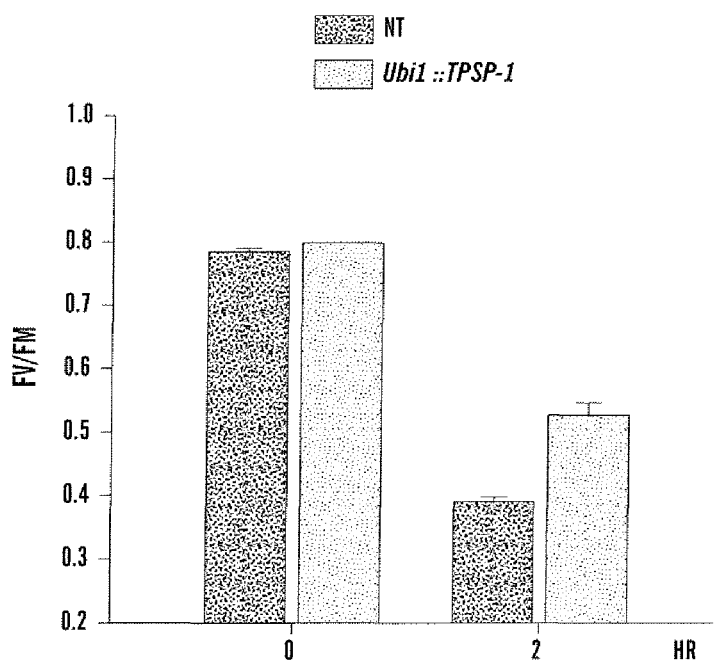
FIG. 4B is a graph showing chlorophyll fluorescence in salt-stress treated Ubi1::TPSP rice plants.
Figure 4C:
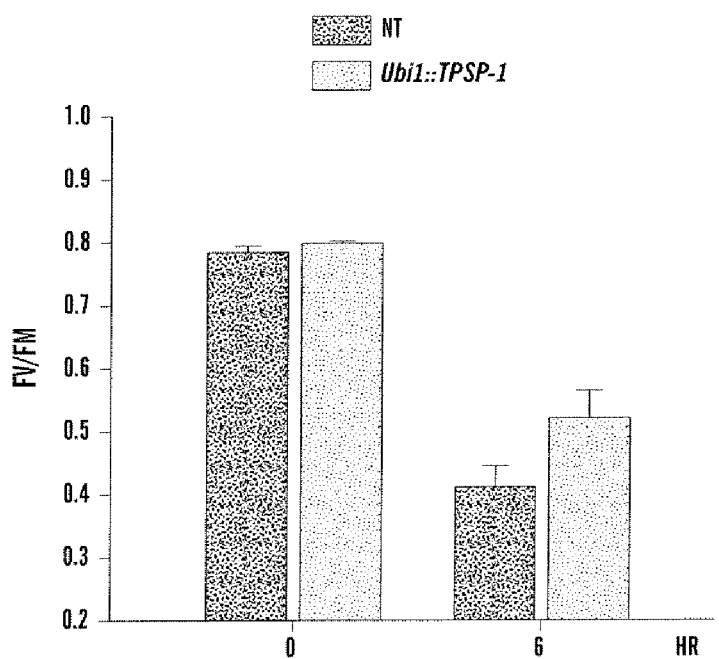
FIG. 4C is a graph showing chlorophyll fluorescence in cold-stress treated Ubi1::TPSP rice plants.
Figure 5A:
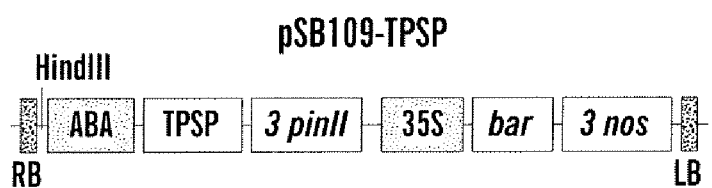
Figure 5B:
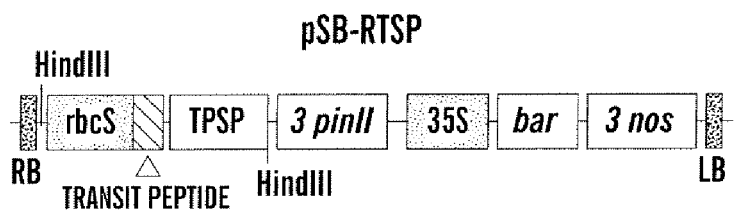
Figure 5D:
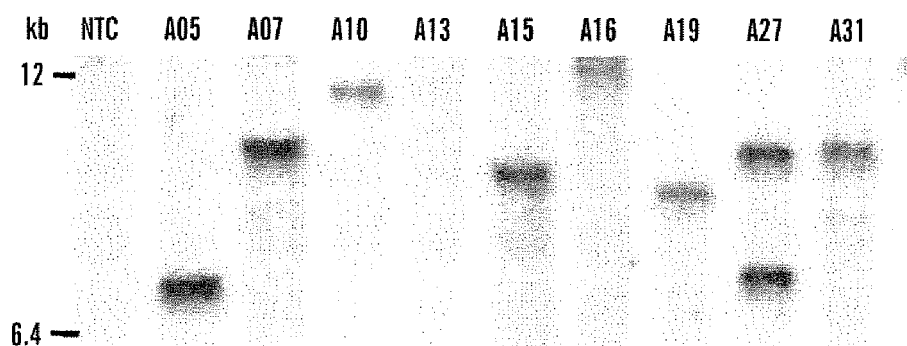
Figure 5E:
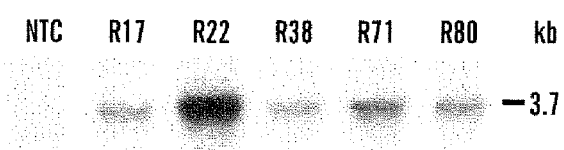
Figure 6A:
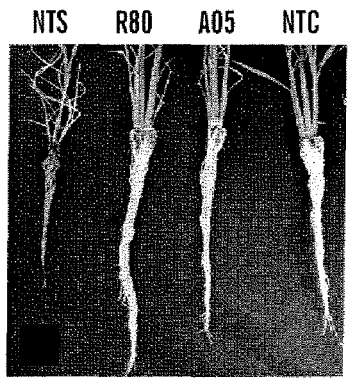
FIGS. 6A-F show the salt tolerance of rice plants and changes in mineral nutrition caused by salt stress.
Figure 6B:
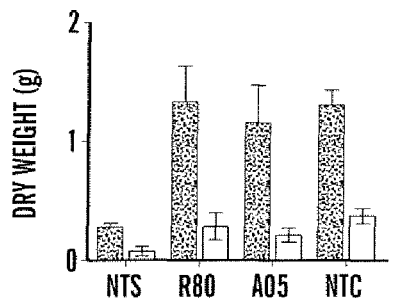
Figure 6C:
Figure 6D:
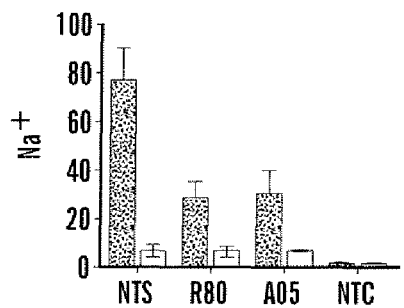
Figure 6E:
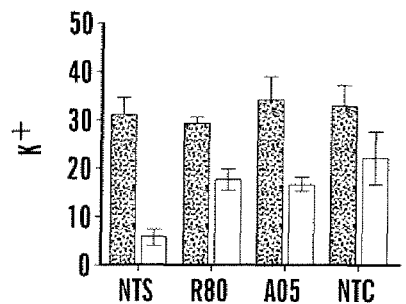
Figure 6F:
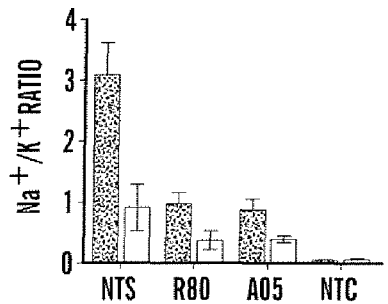
Figure 7C:
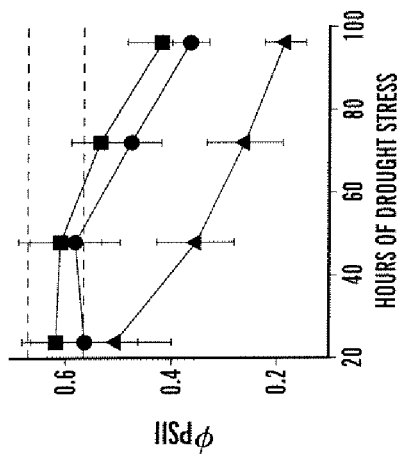
FIGS. 7A-D show the appearance of plants and chlorophyll fluorescence parameters during drought stress. Five-week-old nontransformed and $T_4$ generation transgenic (R80 and A05) seedlings grown in soil were subjected to two cycles of 100 h of drought stress followed by watering for 3 weeks.
Figure 7D:
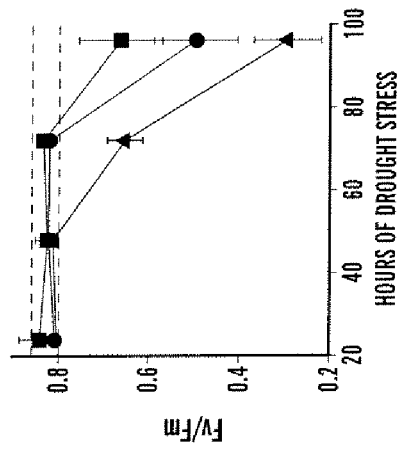
Figure 7A:
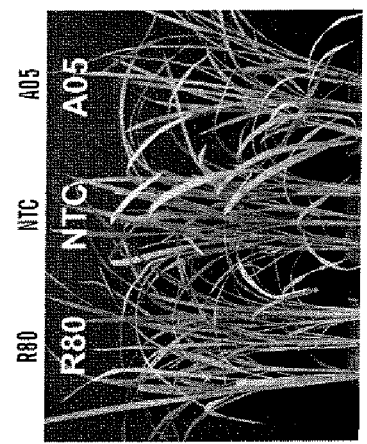
Figure 7B:
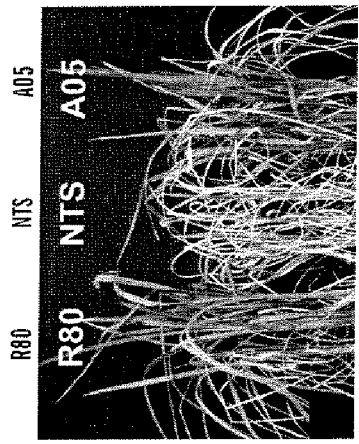

FIGS. 4a, 4b and 4c are the graphs showing chlorophyll fluorescence in dehydration-, salt- and cold-stress treated Ubi1::TPSP rice plants. As can be seen from FIGS. 4a, 4b and 4c, all rice plants treated with dehydration-, salt- and cold-stress showed the Fv/Fm ratios at the level, which is 15-19% higher than that in the control group. Accordingly, it could be confirmed that trehalose plays a role to increase the resistance of rice plants against abiotic stresses.

Example 4

Plasmid Construction for Rice Transformation

Two binary plasmids, pSB109-TPSP and pSB-RTSP, each containing a TPSP fusion gene (Seo et al., "Characterization of a Bifunctional Enzyme Fusion of Trehalose-6-Phosphate Synthetase and Trehalose-6-Phosphate Phosphatase of *Escherichia coli*," *Appl. Environ. Microbiol.*, 66:2484-2490 (2000), which is hereby incorporated by reference in its entirety), were constructed in the pSB11 vector (Komari et al., "Vectors Carrying Two Separate T-DNAs for Co-Transformation of Higher Plants Mediated by *Agrobacterium tumefaciens* and Segregation of Transformants Free from Selection Markers," *Plant J.*, 10: 165-174 (1996), which is hereby incorporated by reference in its entirety) by using standard cloning and plasmid manipulation procedures. The components of the plasmid within the T-DNA region and the selected restriction enzyme sites are shown in FIGS. 5 A, B, and C. The expression cassette in pSB109-TPSP consists of an abscisic acid (ABA)-inducible promoter (Su et al., "Dehydration-Stress-Regulated Transgene Expression in Stably Transformed Rice Plants," *Plant Physiol.*, 117:913-922 (1998), which is hereby incorporated by reference in its entirety) that contains four tandem copies of ABA-inducible element ABRC1 (0.18 kb) coupled with a minimal rice actin 1 promoter (0.18 kb) and an HVA22 intron (0.24 kb). It is linked to the TPSP coding region (2.2 kb), which was constructed by fusing the otsA and otsB genes from *E. coli* after the stop codon of the otsA gene had been removed by PCR (Seo et al., "Characterization of a Bifunctional Enzyme Fusion of Trehalose-6-Phosphate Synthetase and Trehalose-6-Phosphate Phosphatase of *Escherichia coli*," *Appl. Environ. Microbiol.*, 66:2484-2490 (2000), which is hereby incorporated by reference in its entirety) and then ligated to the potato protease inhibitor II gene (pinII) 3' noncoding sequence (1.0 kb). The selection cassette includes the cauliflower mosaic virus 35S promoter (0.74 kb), phosphinothricin acetyltransferase gene (bar, 0.59 kb), and the nopaline synthase gene 3' noncoding sequence (Nos 3', 0.28 kb). In pSB-RTSP, a 1.3-kb fragment of the rice rbcS promoter (Kyozuka et al., "Light-Regulated and Cell-Specific Expression of Tomato rbcS-gusA and Rice rbcS-gusA Fusion Genes in Transgenic Rice," *Plant Physiol.*, 102:991-1000 (1993), which is hereby incorporated by reference in its entirety) with a chloroplast-targeting transit peptide (0.16 kb) is linked to the TPSP coding region; the remaining components are similar to those in pSB109-TPSP. During the cloning and ligation of an ≈3.7-kb DNA fragment containing the rbcS promoter/transit peptide and TPSP fusion gene into the plasmid pSB-RTSP, three additional restriction sites (SacI, SalI, and HindIII) were added between TPSP and 3' pin II. Both the plasmids (pSB109-TPSP and pSB-RTSP) were separately transferred to *Agrobacterium tumefaciens* strain LBA4404 harboring the pSB1 vector (Komari et al., "Vectors Carrying Two Separate T-DNAs for Co-Transformation of Higher Plants Mediated by *Agrobacterium tumefaciens* and Segregation of Transformants Free from Selection Markers," *Plant J.*, 10:165-174 (1996), which is hereby incorporated by reference in its entirety) through triparental mating using the helper plasmid pRK2013. For cocultivation, the bacteria were grown from a single colony in liquid AB medium containing 50 mg/liter spectinomycin at 30° C. for 3 days and were suspended at a density of $3 \times 10^9$ cells per ml in AAM medium (Hiei et al., "Efficient Transformation of Rice (*Oryza sativa* L.) Mediated by *Agrobacterium* and Sequence Analysis of the Boundaries of the T-DNA," *Plant J.*, 6:271-282 (1994), which is hereby incorporated by reference in its entirety) for rice transformation.

Example 5

Production of Transgenic Rice Plants

Mature seeds of *Indica* rice variety PB-1 were dehusked and sterilized in 70% (vol/vol) ethanol for 2-3 min and then transferred into 50% (vol/vol) Clorox solution for 40 min with gentle shaking. The seeds were rinsed several times with sterile water. The sterilized PB-1 seeds were then plated for callus induction on Murashige and Skoog (MS) medium (Sigma) supplemented with 3.0 mg/liter 2,4-dichlorophenoxyacetic acid (2,4-D)/0.2 mg/liter 6-benzylaminopurine (BAP)/300 mg/liter casein hydrolysate (CH)/30 g/liter maltose/3.0 g/liter phytagel, pH 5.8 (MSCl) and grown for 21 days at 25° C. in the dark. Three weeks after callus induction from the scutellar region of the rice embryo, 150 embryogenic calli were immersed in *A. tumefaciens* suspension for 10 min. Infected calli were cocultivated in MSCl medium supplemented with 10 g/liter glucose/100 µM acetosyringone, pH 5.2 (MSCC). After 3 days of cocultivation, calli were washed with sterile water containing 250 mg/liter cefotaxime and blotted on filter paper. The calli were immediately plated on a selection medium, MSCl medium, supplemented with 6 mg/liter bialaphos and 250 mg/liter cefotaxime, pH 5.8 (MSS), and incubated at 25° C. in the dark for 2-3 weeks. The microcalli that had proliferated after the initial selection were further subcultured for two selection cycles on fresh MSS medium every 2 weeks. The actively dividing bialaphos-resistant calli were plated on MS plant regeneration medium containing 2.5 mg/liter BAP/1.0 mg/liter kinetin/0.5 mg/liter naphthaleneacetic acid (NAA)/300 mg/liter CH/30 g/liter maltose/4 mg/liter bialaphos/250 mg/liter cefotaxime/2.0 g/liter phytagel, pH 5.8 (MSPR) and grown at 25° C. for a 10-h light/14-h dark photoperiod for 3-4 weeks. The regenerated plantlets were acclimatized hydroponically in Yoshida nutrient solution (Yoshida et al., *Laboratory Manual for Physiological Studies of Rice*, International Rice Research Institute, Manila, Philippines, pp. 61-66 (1976), which is hereby incorporated by reference in its entirety), for 10 days. Later on, putative primary transformants ($T_0$ generation) were transferred to pots and tested for Basta-herbicide resistance (Roy and Wu, "Arginine Decarboxylase Transgene Expression and Analysis of Environmental Stress Tolerance in Transgenic Rice," *Plant Sci.* 160:869-875 (2001), which is hereby incorporated by reference in its entirety); the transgenic plants were grown to maturity in a greenhouse for further analysis.

Example 6

DNA Blot Hybridization Analysis of Transgenic Rice Plants

Leaves from nontransformed control (NTC) plant, and representative ($T_0$) transformants of nine A-lines (ABA-inducible promoter) and five R-lines (rbcS promoter) that were transformed with the plasmid pSB109-TPSP and pSB-RTSP, respectively, were ground in liquid nitrogen by using a mortar and pestle. Rice genomic DNA was isolated by the guanidine-detergent lysis method by using DNAzolES (Molecular Research Center, Cincinnati) following the manufacturer's instructions. Five micrograms of the genomic DNA was digested overnight with HindIII restriction enzyme, fractionated through 0.8% agarose gel, alkali-transferred onto Hybond N+ nylon membrane (Amersham Pharmacia), and hybridized with an $\alpha$-$^{32}$P-labeled 2.2-kb TPSP fusion gene (Seo et al., "Characterization of a Bifunctional Enzyme Fusion of Trehalose-6-Phosphate Synthetase and Trehalose-6-Phosphate Phosphatase of *Escherichia coli*," *Appl. Environ. Microbiol.*, 66:2484-2490 (2000), which is hereby incorporated by reference in its entirety) as the probe. DNA probe preparation, hybridization, and washing of the membrane were performed as described (Roy and Wu, "Arginine Decarboxylase Transgene Expression and Analysis of Environmental Stress Tolerance in Transgenic Rice," *Plant Sci.* 160:869-875 (2001), which is hereby incorporated by reference in its entirety). The $\alpha$-$^{32}$P-labeled membrane was exposed onto autoradiogram.

Example 7

Detecting Trehalose and Soluble Carbohydrates

Soluble carbohydrates were extracted as described (Goddijn et al., "Inhibition of Trehalase Activity Enhances Trehalose Accumulation in Transgenic Plants," *Plant Physiol.*, 113:181-190 (1997), which is hereby incorporated by reference in its entirety). Extracts from 0.5 g of homogenized fresh leaf tissue were centrifuged (10 min at 3,220×g); supernatants were passed through ion-exchange columns consisting of 1 ml of Amberlite IR-68 (acetate form) layered on 1 ml of Dowex 50W (hydrogen form) to remove charged compounds. After lyophilization, samples were dissolved in HPLC-grade water and subjected to high-performance anion exchange chromatography with pulsed amperometric detection by using a Dionex DX-500 series chromatograph equipped with a Carbopac PA-1 analytical column and a Carbopac PA-1 guard column (Dionex). Carbohydrates were eluted at a flow rate of 1.0 ml per min at 1,400 psi with 100 mM NaOH for 34 min. Major soluble carbohydrates present were quantified by using authentic standard sugars (Sigma). The identity of trehalose in the plant extracts was confirmed by incubating samples with porcine-kidney-derived trehalase enzyme (Sigma).

Example 8

Determination of Salt Stress Tolerance and Plant Mineral Nutrients

Ten seedlings for each $T_4$ generation transgenic line (R22, R38, R80, A05, A07, and A27) and NTC were grown hydroponically (with modest aeration) in Yoshida nutrient solution (Yoshida et al., *Laboratory Manual for Physiological Studies of Rice*, International Rice Research Institute, Manila, Philippines, pp. 61-66 (1976), which is hereby incorporated by reference in its entirety) in a growth chamber at 25±3° C. for a 10-h light/14-h dark photoperiod (photon flux density of 280 µmol photons per m/s) and with relative humidity of 50-60%. After 5 weeks, 50% of the seedlings were subjected to 100 mM NaCl stress (conductivity of 10-12 dS/m). Nutrient solutions were replaced every week. After 4 weeks of continuous salt stress, shoot and root samples were separately harvested for fresh and dry weight determination. For mineral nutrient analysis, 150 mg of ground dry matter was digested in concentrated $HNO_3$ overnight at 120° C. Samples then were dissolved in $HNO_3$:$HClO_4$ (1:1, vol/vol) at 220° C., resuspended in 5% (vol/vol) $HNO_3$, and analyzed for elemental composition of sodium ($Na^+$), potassium ($K^+$), calcium ($Ca^{2+}$), and iron (Fe) by means of simultaneous inductively coupled argon-plasma emission spectrometry (ICP trace analyzer; Plant, Soil, and Nutrition Laboratory, U.S. Department of Agriculture-Agriculture Research Service, Cornell University, Ithaca, N.Y.).

Example 9

Determination of Drought and Low-Temperature Stress Tolerance

Seedlings from six independent $T_4$ transgenic lines and nontransformed line were grown individually in 10-cm×10-cm pots irrigated with Yoshida nutrient solution for 5 weeks before performing the drought- or low-temperature stress experiment. Drought stress (water deficit) was conducted by first withholding irrigation for 3 days to allow the soil in the pot to dry. Then, the first drought cycle of 100 h was initiated, followed by rewatering for 2 days. The drought-stress cycle was repeated for another 100 h, and the plants were allowed to recover by watering every day for 3 weeks. Low-temperature stress was conducted on five-week-old seedlings by exposing them to 10° C. for 72 h under a 10-h light/14-h dark photoperiod (photon flux density of 280 µmol photons per m per s) and a relative humidity of 50-60%; the seedlings were then allowed to recover under normal growth conditions at 25±3° C.

Example 10

Protein Extraction and Immunoblotting

Proteins were extracted from 0.2 g of homogenized fresh leaf tissue in protein extraction buffer (20 mM Tris·HCl, pH 8.0/10 mM EDTA/30 mM NaCl/2 mM phenylmethane sulfonyl fluoride for 1 h at 4° C.). The homogenate was clarified by centrifugation at 12,000×g for 15 min at 4° C. The procedure for immunoblotting was essentially the same as described (Xu et al., "Expression of a Late Embryogenesis Abundant Protein Gene, HVA1, from Barley Confers Tolerance to Water Deficit and Salt Stress in Transgenic Rice," *Plant Physiol.* 110:249-257 (1996), which is hereby incorporated by reference in its entirety). The anti-TPSP protein polyclonal antibody was used at a 1:1,500 dilution for Western blot analysis, using an alkaline phosphatase color reaction for detection of the protein, as per the manufacturer's instruction (Bio-Rad).

Example 11

Chlorophyll Fluorescence Parameters

Fv/Fm and $\phi_{PSII}$ were measured by using a pulse amplitude modulated fluorometer (FMS2, Hansatech Instruments, Pentney King's Lynn, U.K.) to estimate photo-oxidative damage to the Photosystem II (PS II) reaction center and the quantum efficiency of PS II photochemistry under ambient light conditions, respectively, as described (Saijo et al., "Over-Expression of a Single Ca2+-Dependent Protein Kinase Confers Both Cold and Salt/Drought Tolerance on Rice Plants," *Plant*

J. 23:319-327 (2000), which is hereby incorporated by reference in its entirety). Measurements were made on the youngest, fully expanded leaves. Measurements of $\phi_{PSII}$ were first determined under ambient light; the same leaves were then dark-adapted for 10 min before measurement of Fv/Fm.

Example 12

Transgenic Rice Plants with Enhanced Trehalose Levels Are Phenotypically Normal and Fertile Two plasmid constructs, pSB109-TPSP (FIGS. 5A, C) and pSB-RTSP (FIGS. 5 B, C), each containing the TPSP fusion gene, were introduced into *Indica* rice cells of PB-1 by *Agrobacterium*-mediated gene transfer (Hiei et al., "Efficient Transformation of Rice (*Oryza sativa* L.) Mediated by *Agrobacterium* and Sequence Analysis of the Boundaries of the T-DNA," *Plant J.*, 6:271-282 (1994), which is hereby incorporated by reference in its entirety). In the plasmid construct pSB109-TPSP, an ABA and stress-inducible promoter (Su et al., "Dehydration-Stress-Regulated Transgene Expression in Stably Transformed Rice Plants," *Plant Physiol.*, 117:913-922 (1998), which is hereby incorporated by reference in its entirety) drives the fusion gene for cytosolic expression. In the other plasmid, pSB-RTSP, the light-regulated promoter (Kyozuka et al., "Light-Regulated and Cell-Specific Expression of Tomato rbcS-gusA and Rice rbcS-gusA Fusion Genes in Transgenic Rice," *Plant Physiol.*, 102:991-1000 (1993), which is hereby incorporated by reference in its entirety) of the Rubisco small subunit gene, rbcS, from *Oryza sativa* with a transit peptide drives the fusion gene for chloroplast targeting in the leaf mesophyll cells. A large number of putative transgenic PB-1 plants ($T_0$ generation) were regenerated (Table 1); these plants included 28 A-lines (ABA-inducible promoter) and 76 R-lines (rbcS promoter).

TABLE 1

Efficiency of rice transformation using *Agrobacterium tumefaciens* strain LBA 4404 (pSB1) containing the TPSP fusion gene in plasmids pSB109-TPSP and pSB-RTSP

| Plasmid | pSB109-TPSP | pSB-RTSP |
|---|---|---|
| Promoter | ABA and stress-inducible | Rice rbcS with transit peptide |
| Expression Target | Cytosolic | Chloroplast |
| No. of calli co-cultivated | 150 | 150 |
| No. of bialophos resistant calli | 41/150 | 118/150 |
| No. of plants regenerated | 29/41 | 89/118 |
| No. of basta resistant plants | 28/29 | 76/89 |
| No. of fertile $T_0$ lines | 22 (79%) | 68 (90%) |

Numbers in parenthesis indicate percentage of completely fertile plants.

Integration of the TPSP transgene was confirmed by DNA-blot hybridization analysis (FIGS. 5 D and E). Based on the T-DNA junction fragment analysis, ≈40% of the transgenic plants transformed with either of the plasmids harbor a single copy, and 35-45% of plants harbor two or three copies of the transgene.

Figure 10A:
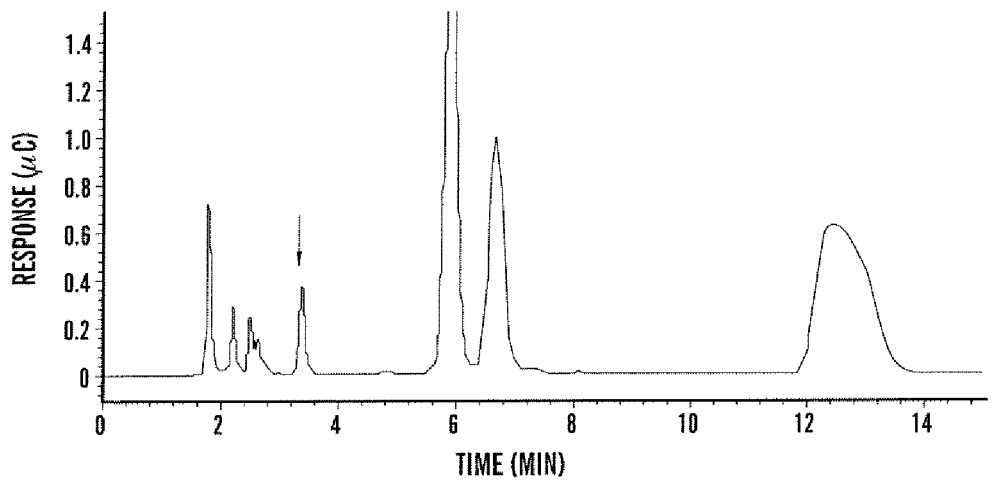
FIGS. 10A and B show high-performance anion exchange chromatography with pulsed amperometric detection (HPAEC-PAD) analysis of trehalose accumulation in a transgenic rice line.
Figure 10B:
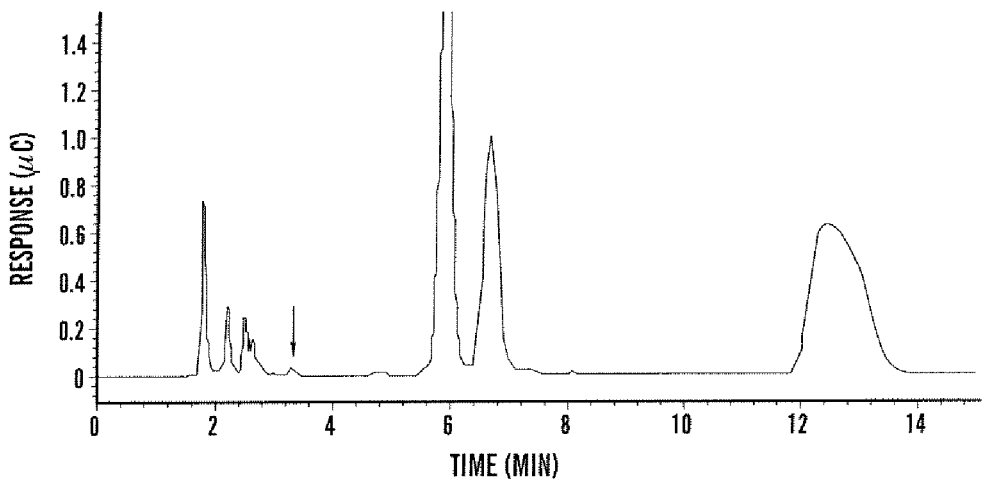
In FIG. 10B, the chromatogram shows the PAD-response profile of the same sample after digestion with trehalase enzyme. Arrow indicates the trehalose peak.

Most of the 90 independent primary transformants ($T_0$) that contained a low copy number of the transgene showed a normal phenotype and were completely fertile. In contrast to previous reports that used constitutive promoters driving individual TPS and/or TPP genes, the use of stress-inducible or tissue-specific promoters in this work appears to minimize the negative effects of the transgene on plant growth. The $T_0$ plants were self-pollinated to obtain segregating $T_1$ progeny for genetic and HPLC analysis. Forty-five transgenic lines showed a segregation pattern of 3:1 for the basta-herbicide resistance marker gene. HPLC analysis of leaf extracts showed that transgenic lines had a trehalose content that was between three times and eight times that of the nontransgenic plants (17±5 μg of trehalose per g of fresh weight). The identity of trehalose in the plant tissue extracts was confirmed by incubating samples in porcine trehalase followed by chromatographic analysis of the monosaccharide products (FIG. 10). Physiological experiments were conducted for abiotic stress tolerance on homozygous plants through the $T_4$ generation, because gene silencing has been reported to occur in the $T_3$ generation, even though $T_2$ and $T_1$ generation plants were not silenced (Iyer et al., "Transgene Silencing in Monocots," *Plant Mol. Biol.*, 43:323-346 (2000), which is hereby incorporated by reference in its entirety). The results from many independent transgenic lines were consistent for salt- and drought-stress tolerance in each generation, except in few transgenic lines which had multiple copies of the transgene.

Example 13

Transgenic Rice Plants Are Salt Tolerant and Maintain Balanced Mineral Nutrition The $T_4$ transgenic plants with either one or two copies of the transgene showed markedly enhanced salt tolerance during and subsequent to 4 weeks of 100 mM NaCl treatment under hydroponic growth conditions. Six independent transgenic plant lines (three A-lines and three R-lines) were analyzed in detail. For clarity of presentation, results from two representative transgenic lines (R80 and A05) are shown (FIG. 6); results for the other four lines were very similar to the two lines presented. After prolonged exposure to salt stress, almost all of the transgenic plants survived and displayed vigorous root and shoot growth. In contrast, all of the nontransformed stressed (NTS) plants were either dead or nearly dead because of severe salt damage to the leaves and concomitant loss of chlorophyll. Transgenic plants developed longer and thicker roots than NTS plants after salt stress (FIG. 6 A). Salt stress severely inhibited the growth of shoot and roots of NTS plants, as indicated by their lower dry weights compared with NTC plants. Shoot and root dry weights of both the transgenic lines (FIG. 6 B) approached those of NTC plants, and, after removal of salt stress, the transgenic plants were able to grow, flower, and set normal viable seeds. To determine whether the TPSP gene product was present in the salt-stressed plants, total protein was isolated from the leaf samples for Western blot analysis. Immunoblot analysis using polyclonal antibodies raised against the fusion protein showed the presence of a protein with the expected apparent molecular mass of 88 kDa only in the transgenic plants (FIG. 6 C).

To assess how trehalose accumulation in transgenic rice affected plant mineral nutrition during salt stress, shoot and root mineral content for the six independent transgenic lines and two nontransgenic lines were determined by using inductively coupled plasma emission spectrometry (Table 2).

TABLE 2

Plant mineral nutrient content (sodium, potassium, calcium, and iron ions) in shoots and roots of transgenic lines (R22, R38, R80 A05, A07, and A27) and nontransformed control lines with or without salt stress

| Line | Na Shoot | Na Root | K Shoot | K Root | Ca Shoot | Ca Root | Fe Shoot | Fe Root |
|---|---|---|---|---|---|---|---|---|
| Nonstress conditions | | | | | | | | |
| NTC-1 | 1.4 ± 0.3 | 1.2 ± 0.1 | 33 ± 8 | 18 ± 6 | 2.5 ± 0.6 | 0.6 ± 0.1 | 0.13 ± 0.08 | 2.8 ± 1.5 |
| NTC-2 | 1.1 ± 0.3 | 1.3 ± 0.3 | 33 ± 3 | 15 ± 2 | 2.3 ± 0.1 | 0.7 ± 0.1 | 0.13 ± 0.04 | 3.5 ± 0.7 |
| R22 | 1.2 ± 0.3 | 1.1 ± 0.4 | 30 ± 2 | 21 ± 1 | 2.5 ± 0.5 | 1.6 ± 0.2 | 0.20 ± 0.09 | 6.1 ± 3.0 |
| R38 | 0.9 ± 0.2 | 1.8 ± 0.2 | 35 ± 5 | 23 ± 4 | 2.3 ± 0.5 | 1.0 ± 0.3 | 0.16 ± 0.03 | 3.7 ± 0.4 |
| R80 | 1.2 ± 0.2 | 1.5 ± 0.2 | 44 ± 1 | 23 ± 1 | 2.8 ± 0.7 | 0.5 ± 0.1 | 0.28 ± 0.01 | 4.3 ± 1.1 |
| A05 | 1.0 ± 0.3 | 1.5 ± 0.8 | 45 ± 1 | 22 ± 4 | 2.7 ± 0.5 | 0.6 ± 0.1 | 0.21 ± 0.04 | 4.3 ± 0.4 |
| A07 | 2.2 ± 0.7 | 1.1 ± 0.2 | 45 ± 1 | 24 ± 1 | 3.7 ± 1.2 | 0.9 ± 0.2 | 0.25 ± 0.07 | 4.3 ± 0.2 |
| A27 | 1.9 ± 0.4 | 1.0 ± 0.3 | 47 ± 4 | 20 ± 1 | 2.4 ± 0.8 | 1.5 ± 0.2 | 0.19 ± 0.01 | 5.1 ± 2.9 |
| Salt-stress conditions (100 mM NaCl) | | | | | | | | |
| NTS-1 | 77 ± 13 | 7 ± 3 | 31 ± 4 | 6 ± 2 | 4.4 ± 0.8 | 1.8 ± 0.3 | 0.25 ± 0.08 | 9.3 ± 2.7 |
| NTS-2 | 87 ± 17 | 4 ± 1 | 30 ± 2 | 3 ± 1 | 5.6 ± 0.5 | 1.7 ± 0.3 | 0.24 ± 0.05 | 8.3 ± 3.4 |
| R22 | 34 ± 10 | 6 ± 2 | 26 ± 2 | 16 ± 2 | 4.6 ± 0.7 | 1.0 ± 0.3 | 0.47 ± 0.11 | 5.8 ± 2.3 |
| R38 | 24 ± 10 | 7 ± 1 | 30 ± 2 | 17 ± 4 | 4.1 ± 0.8 | 0.5 ± 0.1 | 0.42 ± 0.07 | 4.7 ± 1.5 |
| R80 | 28 ± 7 | 6 ± 2 | 29 ± 2 | 17 ± 2 | 4.2 ± 0.6 | 0.7 ± 0.1 | 0.47 ± 0.08 | 6.8 ± 2.6 |
| A05 | 30 ± 10 | 6 ± 1 | 34 ± 5 | 17 ± 1 | 4.2 ± 0.8 | 0.5 ± 0.2 | 0.46 ± 0.03 | 7.8 ± 1.4 |
| A07 | 24 ± 8 | 7 ± 1 | 29 ± 2 | 18 ± 3 | 2.7 ± 0.5 | 0.5 ± 0.1 | 0.48 ± 0.04 | 5.3 ± 0.8 |
| A27 | 18 ± 7 | 7 ± 3 | 29 ± 4 | 20 ± 1 | 3.0 ± 0.5 | 0.5 ± 0.3 | 0.45 ± 0.05 | 5.5 ± 1.4 |

The ionic concentration is presented as mg/g shoot or roots dry weight.
Values are the means ± SD (n = 5).

After continuous salt stress (100 mM NaCl) for 4 weeks, NTS plants showed a very large increase in $Na^+$ content in both shoots and roots compared with NTC, whereas the increase in the shoots of all of the transgenic plants was much smaller (FIG. 6 D). The $Na^+$ content of transgenic plant shoots was only 30-35% of the NTS plants after salt stress. The observed differences in shoot $Na^+$ content between transgenic and NTS plants could be caused in part by a growth dilution because of the much faster growth rate of the transgenic plants under salt stress. Alternatively, trehalose might have played a direct or indirect role in maintaining ion selectivity and, thus, facilitating cellular $Na^+$ exclusion. This possibility is consistent with the report that in salt-stressed rice seedlings, the accumulation of $Na^+$ in leaf tissues was not prevented by exogenous proline. In contrast, treatment with exogenous trehalose significantly reduced the salt-induced accumulation of $Na^+$ in the leaves (Garcia et al., "Effects of Osmoprotectants Upon NaCl Stress in Rice," *Plant Physiol.*, 115:159-169 (1997), which is hereby incorporated by reference in its entirety).

Transgenic lines R80 and A05 maintained shoot to root $K^+$ homeostasis both under nonstress and salt-stress conditions (Table 2). After salt stress, the levels of shoot and root $K^+$ content in transgenic plants was similar to the nonstressed controls, while a fourfold decrease in root $K^+$ in the NTS plants was seen (FIG. 6 E). Thus, the transgenic plants were able to maintain a higher level of selectivity for $K^+$ over $Na^-$ uptake in the roots and $Na^+$ exclusion from the shoots compared with the NTS plants. The maintenance of the $Na^+/K^+$ ratio in both shoot and roots of transgenic plants (FIG. 6 F) correlated with nearly normal plant growth and may be the basis for minimizing $Na^-$ toxicity under salt stress. It is generally accepted that the maintenance of $Na^+/K^+$ homeostasis is an important aspect of salt tolerance (Rus et al., "AtHKT1 is a Salt Tolerance Determinant that Controls $Na^+$ Entry into Plant Roots," *Proc. Natl. Acad. Sci. USA,* 98:14150-14155 (2001) and Epstein, "Plant Biology: How Calcium Enhances Plant Salt Tolerance," *Science,* 280:1906-1907 (1998), which are hereby incorporated by reference in their entirety).

Several other changes in plant mineral status that may have played indirect roles in stress tolerance were seen in the transgenic lines compared with the NTCs. It was found that salt stress led to a significant increase in root and shoot $Ca^{2+}$ content in the NTS lines, whereas in the transgenic lines, this Na-mediated increase in $Ca^{2+}$ content was only observed in the shoots and not the roots (Table 2). This rise in $Ca^{2+}$ may be caused by alterations in the ion selectivity of the transporters at high concentrations of $Na^+$ (Epstein, "Plant Biology: How Calcium Enhances Plant Salt Tolerance," *Science,* 280:1906-1907 (1998), which is hereby incorporated by reference in its entirety). Significantly higher levels of shoot Fe ion content were also found in the transgenic lines compared with the NTCs (Table 2). It has been well documented that Fe, Cu, and Zn ions are essential for the function of critical antioxidant enzymes such as the superoxide dismutases that play a role in scavenging reactive oxygen species during a number of abiotic stresses (Epstein, "Plant Biology: How Calcium Enhances Plant Salt Tolerance," *Science,* 280:1906-1907 (1998), Alscher et al., "Role of Superoxide Dismutases (SODs) in Controlling Oxidative Stress in Plants," *J. Exp. Bot.,* 53:1331-1341 (2002), which are hereby incorporated by reference in their entirety). In general, the relationship between salt stress and plant mineral content is complex, and the links between elevated trehalose content and improved mineral status during salt stress are not known.

Example 14

Transgenic Rice Plants are Water Stress Tolerant

To study drought tolerance, 5-week-old nontransformed and transgenic seedlings grown in soil were subjected to two cycles of 100 h of drought stress. After the drought treatments, all 15 plants of each line showed wilting and drought-induced rolling of the young leaves. Nontransgenic plants exhibited rolling of leaves within 48 h of the stress as compared with considerably fewer visual symptoms in transgenic plants during the same time period. After two cycles of 100 h of drought stress and subsequent watering for 3 weeks, the growth of both the transgenic lines, R80 and A05 (FIG. 7 B), were almost identical to nonstressed control plant (FIG. 7 A). In contrast, the growth of the drought-stressed NTS was severely inhibited (FIG. 7 B).

Example 15

Transgenic Rice Plants Produced Increased Amounts of Trehalose and Other Soluble Carbohydrates To evaluate whether trehalose accumulation in plants might act as a positive regulator of stress tolerance, the levels of trehalose and other soluble carbohydrates were measured (Table 3).

TABLE 3

Levels of trehalose, glucose, fructose, sucrose, and total soluble carbohydrate content in shoots of nontransformed (NT) and six transgenic rice lines (R22, R38, R80 A05, A07, and A27) grown under no stress, salt-stressed (100 mM NaCl for 4 weeks), or drought-stressed (after first 100-hr drought stress cycle) conditions

| Line | Trehalose | Glucose | Fructose | Sucrose | Total |
|---|---|---|---|---|---|
| Nonstress Conditions | | | | | |
| NTC-1 | 17 ± 5 | 3.9 ± 0.17 | 3.4 ± 0.61 | 46 ± 3.7 | 53 ± 4.4 |
| NTC-2 | 16 ± 6 | 3.8 ± 0.36 | 3.1 ± 0.70 | 45 ± 5.1 | 52 ± 5.6 |
| R22 | 98 ± 14 | 5.0 ± 0.39 | 4.5 ± 0.74 | 51 ± 1.3 | 61 ± 2.2 |
| R38 | 71 ± 11 | 4.9 ± 0.27 | 4.3 ± 0.65 | 49 ± 3.6 | 58 ± 4.1 |
| R80 | 55 ± 8 | 5.5 ± 0.30 | 4.9 ± 0.79 | 54 ± 4.5 | 64 ± 6.0 |
| A05 | 48 ± 7 | 5.6 ± 0.33 | 5.2 ± 0.85 | 53 ± 9.6 | 64 ± 10 |
| A07 | 62 ± 8 | 5.6 ± 0.44 | 5.1 ± 0.89 | 60 ± 8.3 | 71 ± 9.9 |
| A27 | 54 ± 9 | 5.2 ± 0.41 | 4.6 ± 0.69 | 52 ± 6.7 | 62 ± 7.8 |
| Drought-Stress Conditions | | | | | |
| NTS-1 | 53 ± 11 | 4.7 ± 0.75 | 4.0 ± 0.86 | 45 ± 2.6 | 54 ± 3.8 |
| NTS-2 | 47 ± 8 | 4.6 ± 0.47 | 3.5 ± 0.95 | 49 ± 3.6 | 57 ± 4.7 |
| R22 | 156 ± 19 | 4.9 ± 0.49 | 3.7 ± 0.78 | 57 ± 2.3 | 65 ± 3.5 |
| R38 | 257 ± 26 | 5.6 ± 0.66 | 4.8 ± 0.47 | 57 ± 6.6 | 68 ± 7.2 |
| R80 | 163 ± 23 | 4.3 ± 1.24 | 3.1 ± 0.81 | 51 ± 4.2 | 59 ± 4.9 |
| A05 | 508 ± 48 | 3.7 ± 0.51 | 2.3 ± 0.41 | 60 ± 5.6 | 67 ± 6.4 |
| A07 | 474 ± 103 | 4.0 ± 0.83 | 2.6 ± 0.71 | 56 ± 8.1 | 63 ± 10 |
| A27 | 401 ± 69 | 3.8 ± 0.42 | 2.8 ± 0.39 | 27 ± 2.4 | 34 ± 3.1 |
| Salt-Stress Conditions | | | | | |
| NTS-1 | 29 ± 6 | 3.5 ± 0.08 | 3.0 ± 0.04 | 35 ± 2.7 | 42 ± 3.9 |
| NTS-2 | 34 ± 6 | 3.1 ± 0.11 | 2.6 ± 0.03 | 37 ± 2.7 | 42 ± 4.0 |
| R22 | 69 ± 8 | 4.2 ± 0.12 | 4.0 ± 0.08 | 36 ± 2.1 | 44 ± 2.7 |
| R38 | 130 ± 19 | 5.1 ± 0.47 | 5.2 ± 0.12 | 38 ± 2.4 | 48 ± 3.1 |
| R80 | 76 ± 12 | 4.2 ± 0.15 | 3.9 ± 0.10 | 42 ± 3.0 | 50 ± 3.8 |
| A05 | 91 ± 13 | 4.0 ± 0.14 | 3.3 ± 0.10 | 44 ± 4.7 | 51 ± 5.7 |
| A07 | 75 ± 8 | 3.0 ± 0.12 | 2.3 ± 0.09 | 34 ± 2.5 | 40 ± 3.1 |
| A27 | 143 ± 18 | 2.8 ± 0.14 | 1.9 ± 0.10 | 35 ± 4.9 | 40 ± 5.8 |

Means ± SD (n = 3) are presented.
Soluble carbohydrate content data is presented as mg/g shoot fresh weight, except in the case of trehalose, where it is presented as μg/g fresh weight.

Figure 8:
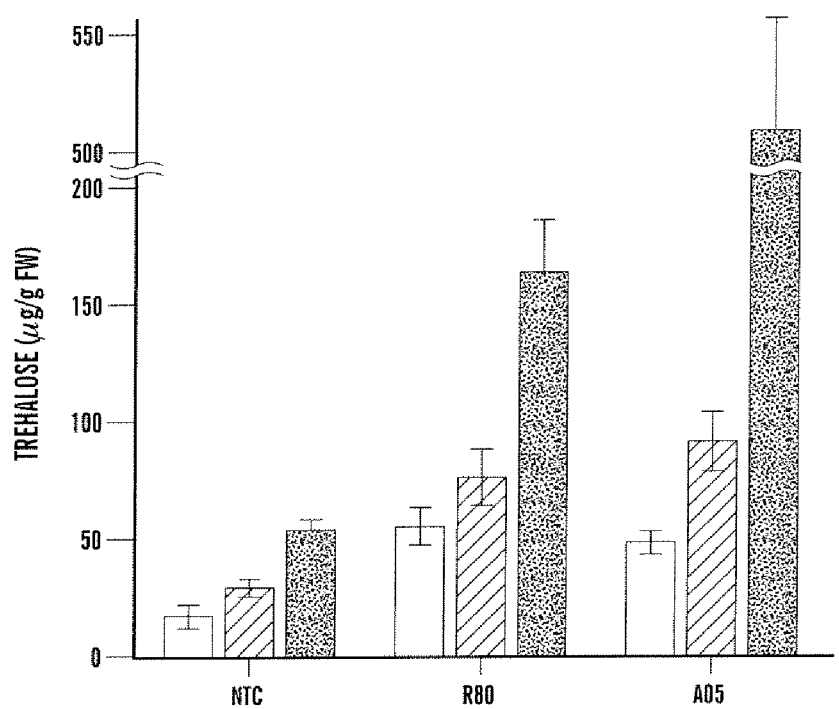
FIG. 8 shows trehalose content in shoots of transgenic (R80 and A05) and nontransgenic plants with or without stress. Trehalose accumulation under nonstressed (white bars), salt-stressed (100 mM NaCl for 4 weeks, hatched bars), or drought-stressed (100 h, black bars) conditions.

A low but significant amount of trehalose was detected in the shoots (17 μg/g fresh weight) of NTC plants; these levels increased significantly under salt or drought stresses. The transgenic plants grown under control conditions exhibited trehalose levels comparable with the NTS plants (FIG. 8). After salt stress, the transgenic lines (R80 and A05) showed 2.5-3 times higher shoot trehalose levels compared with NTS plants, whereas after drought stress, trehalose levels in the transgenic lines increased 3- to 9-fold (FIG. 8). Despite the similarities in tolerance levels exhibited by transgenic plants engineered to increase trehalose synthesis in either the cytosol or chloroplast, R-lines showed considerable protection at much lower trehalose concentrations during drought stress (Table 3). In general, there was no obvious relationship between trehalose accumulation and stress tolerance among the transgenic lines evaluated. On the other hand, the difference in trehalose levels between the transgenic and nontransgenic lines clearly correlates with increased tolerance to abiotic stress.

Example 16

Transgenic Rice Plants Show Improved Photosystem II Function

Figure 11A:
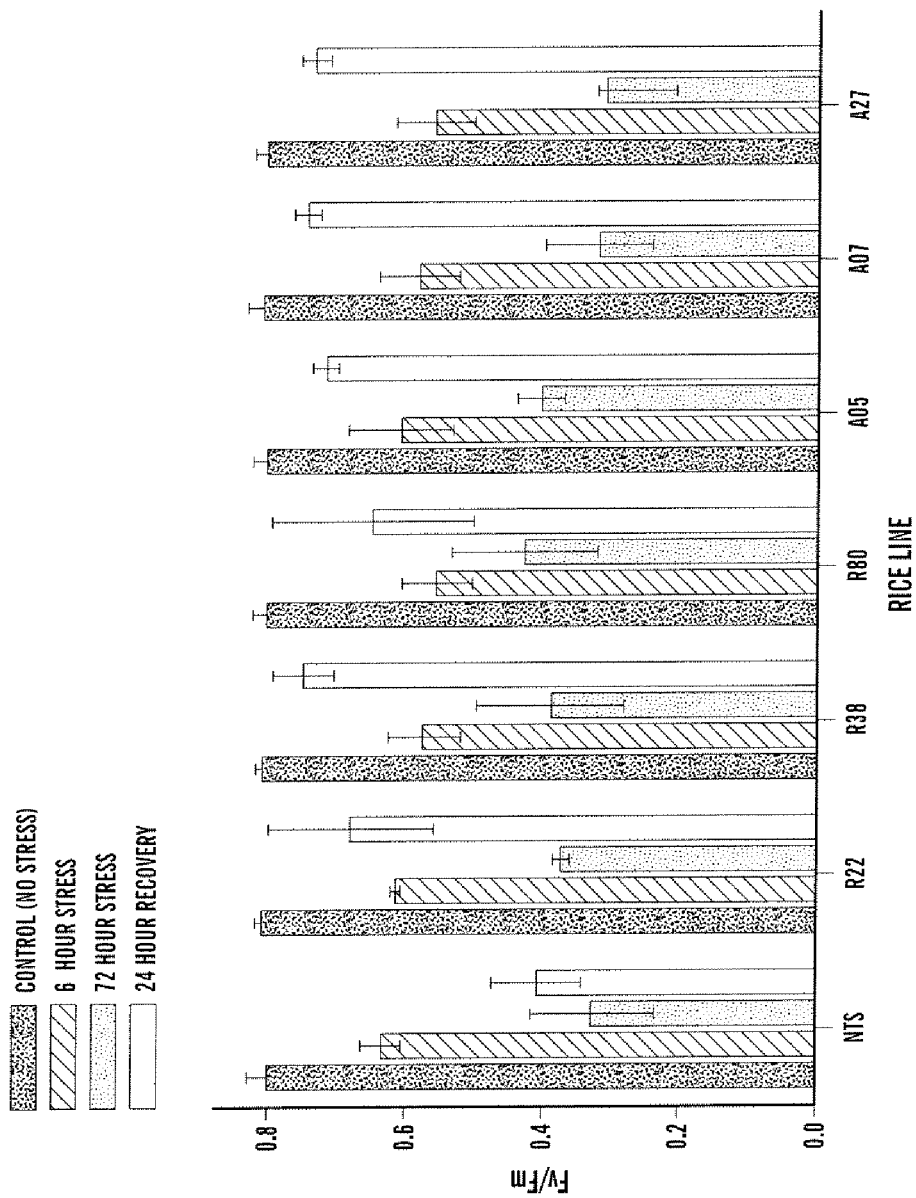
FIGS. 11A and B show changes in the activity of photosystem II ($\phi_{PSII}$) and ratio of variable to maximum fluorescence yields (Fv/Fm) during low-temperature stress, respectively. Five-week-old nontransformed and $T_4$ generation transgenic lines (R22, R38, R80 A05, A07, and A27) seedlings were exposed to 10° C. for 72 h under a 10-h light/14-h dark photoperiod (photon flux density of 280 μmol photons $m^{-2}s^{-1}$) and a relative humidity of 50-60% and then allowed to recover under normal growth conditions at 25±3° C. for 24 h. Activity of $\phi_{PSII}$ and Fv/Fm were monitored for different time intervals during and after the low-temperature stress. Data represent means±SD (n=5) from independent plants.
Figure 11B:
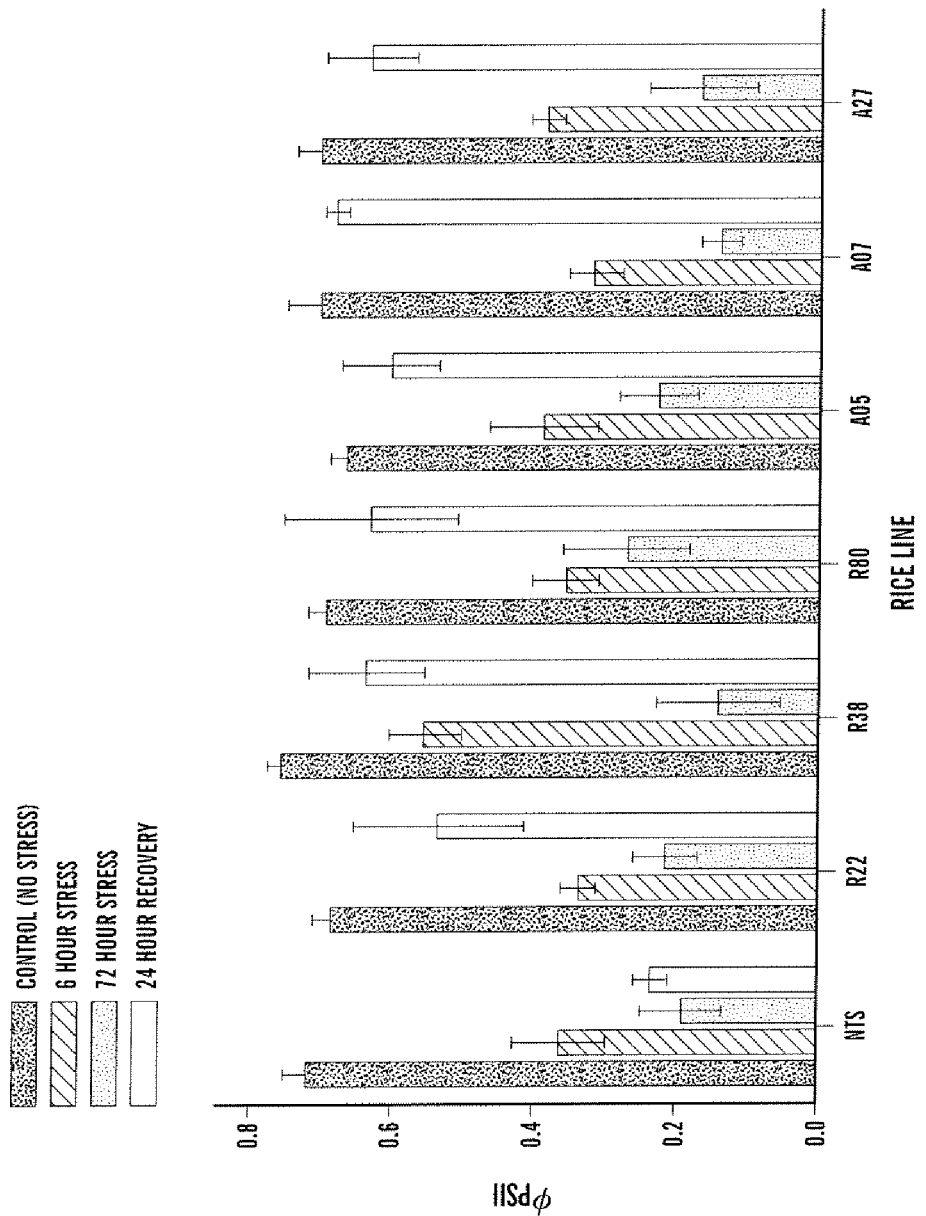
FIG. 11 A shows Fv/Fm.

During many different abiotic stresses, a reduction in photosynthesis and the subsequent production of reactive oxygen species are thought to be a major contributor to decreased plant performance and photooxidative damage. The effects of increased trehalose accumulation on photosynthesis during drought stress were assessed by determination of the quantum yield of PS II photochemistry ($\phi_{PSII}$) by using in vivo chlorophyll fluorescence techniques (Saijo et al., "Over-Expression of a Single $Ca^{2+}$-Dependent Protein Kinase Confers Both Cold and Salt/Drought Tolerance on Rice Plants," Plant J., 23:319-327 (2000), which is hereby incorporated by reference in its entirety). $\phi_{PSII}$ is a measure of the photosynthetic performance of the plant under ambient light conditions. After the first cycle of 100 h of drought stress, the quantum yield of PS II photochemistry in NTS plants decreased by ≈68%, whereas the activity of the two best-performing transgenic lines (R80 and A05) only decreased by 29-37% compared with the nonstressed controls (FIG. 7 C. Similarly, drought-induced decreases in the fluorescence parameter Fv/Fm, which is a measure of accumulated photo-oxidative damage to PS II, were considerably smaller in the transgenic lines than in the NTS plants (FIG. 7 D). In other independent experiments, similar results were obtained for both low-temperature stress (FIG. 11) and salt stress, indicating the common role that maintenance of photosynthetic capacity plays in tolerance to these stresses.

Example 17

Transgenic Rice Plants Have Increased Capacity Under Nonstress Conditions

Improved photosynthesis under abiotic stress conditions is known to limit photo-oxidative damage and permit continued growth (Owens, "Processing of Excitation Energy by Antenna Pigments," in Photosynthesis and the Environment, Baker, ed., Kluwer, Dordrecht, The Netherlands, pp. 1-23 (1996), which is hereby incorporated by reference in its entirety) and is clearly suggested by the data in FIG. 7. Under the same conditions, transgenic plants exhibited soluble carbohydrate levels that were ≈20% higher than those of corresponding NTC plants, including subtle changes in levels of glucose, fructose, and sucrose (Table 3). Both of these results are consistent with the suggestion that trehalose may be involved in sugar sensing and modulating carbon metabolism (Goddijn et al., "Trehalose Metabolism in Plants," Trends Plant Sci., 4:315-319 (1999), Thevelein and Hohmann, "Trehalose Synthase: Guard to the Gate of Glycolysis in Yeast?" Trends Biochem. Sci., 20:3-10 (1995), which are hereby incorporated by reference in their entirety). The ability of trehalose to modulate photosynthetic capacity has been demonstrated recently (Paul et al., "Enhancing Photosynthesis with Sugar Signals," Trends Plant Sci., 6:197-200 (2001), which is hereby incorporated by reference in its entirety) in transgenic tobacco plants expressing *E. coli* trehalose biosynthetic genes. Plants with enhanced TPS expression exhibited a higher photosynthesis per unit of leaf area than nontransgenic controls, whereas those over-expressing TPP showed diminished rates of photosynthesis. These data lead them to conclude that it is trehalose-6-P and not trehalose that is modulating photosynthetic capacity (Paul et al., "Enhancing Photosynthesis with Sugar Signals," *Trends Plant Sci.*, 6:197-200 (2001), which is hereby incorporated by reference in its entirety).

Figure 9:
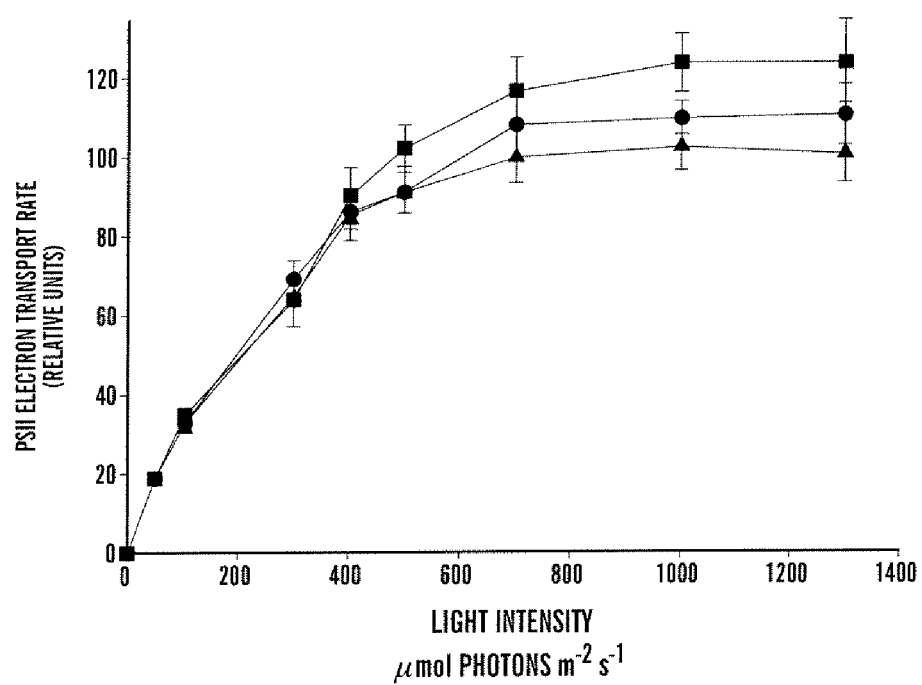
FIG. 9 shows photosystem II electron transport rate in nontransformed and two independent, fifth generation transgenic plants grown under control conditions. The electron transport rate under increasing irradiance was calculated from chlorophyll fluorescence measurements on the youngest fully expanded leaf of NTC (▲), R80 (■), and A05 (●) at 360 ppm of $CO_2$, 25° C., and 50% relative humidity after 10 weeks of growth. Values are the means±SD (n=9). Data are normalized to the average light-saturated rate of the nontransgenic control plants.

FIG. 9 shows the light intensity dependence of PS II electron transport rates, as determined by $\phi_{PSII}$ measurements (Saijo et al., "Over-Expression of a Single $Ca^{2+}$-Dependent Protein Kinase Confers Both Cold and Salt/Drought Tolerance on Rice Plants," *Plant J.* 23:319-327 (2000), which is hereby incorporated by reference in its entirety) for nontransgenic rice and transgenic lines R80 and A05 measured under control (nonstress) conditions. Although the differences in photosynthesis are small at limiting light intensities, at light saturation, the rates of photosynthesis in the transgenic plants are 5-15% higher than in the NTCs. At light saturation, photosynthetic rate is limited by the capacity of the dark reactions, in particular, the Calvin cycle and triose phosphate utilization in the cytoplasm (Owens, "Processing of Excitation Energy by Antenna Pigments," in *Photosynthesis and the Environment*, Baker, ed., Kluwer, Dordrecht, The Netherlands, pp. 1-23 (1996), which is hereby incorporated by reference in its entirety). Together with the observed higher levels of soluble carbohydrate under both stress and nonstress conditions (Table 3), the elevated levels of light-saturated photosynthesis in the transgenic plants supports the suggestion that in plants, trehalose acts as a regulator of sugar sensing and, thus, the expression of genes associated with carbon metabolism (Paul et al., "Enhancing Photosynthesis with Sugar Signals," *Trends Plant Sci.*, 6:197-200 (2001), which is hereby incorporated by reference in its entirety). The presence of a higher capacity for photosynthesis before stress provides a larger sink for the products of photosynthesis during stress, thus limiting the extent of excess-light-induced photooxidative damage and accounting, in part, for the more vigorous growth of the transgenic lines during stress. Interestingly, the higher efficiency of trehalose synthesis by the TPSP fusion gene product (Seo et al., "Characterization of a Bifunctional Enzyme Fusion of Trehalose-6-Phosphate Synthetase and Trehalose-6-Phosphate Phosphatase of *Escherichia coli*," *Appl. Environ. Microbiol.*, 66:2484-2490 (2000), which is hereby incorporated by reference in its entirety) would suggest that trehalose, rather than trehalose-6-P is leading the enhanced capacity for photosynthesis.

Example 18

Production of Transgenic Wheat Plants

Immature embryos were isolated from greenhouse-grown wheat (*Triticum aestivum* L.) cv. Bob White spring wheat variety and precultured for 1-4 days in the dark on modified MS medium before bombardment, as reported by Weeks et al., "Rapid Production of Multiple Independent Lines of Fertile Transgenic Wheat (*Triticum aestivum*), *Plant Physiol.* 102:1077-1084 (1993), which is hereby incorporated by reference in its entirety. Preparation of gold particles and coating with plasmid DNA was carried out based on the manufacturer's instructions (Bio-Rad, Hercules, Calif., USA). Osmotic treatment of target tissue before and after bombardment was performed. Bombarded tissue was placed on the same culture medium supplemented with 5 mg $l^{-1}$ bialaphos (a gift from Dr. H. Anzai, Meiji Seika Kaisha, Japan) for 4 weeks at 25° C. in the dark. Bialaphos-resistant calli were transferred to regeneration medium (MS medium containing 2% sucrose, 0.15 mg $l^{-1}$ thidiazuron and 1 mg $l^{-1}$ bialaphos) for 2-3 weeks at 25° C. under a 16 h photoperiod (66 µmol m–2 $s^{-1}$). After ≈2 weeks, regenerated shoots were transferred to Magenta boxes (Sigma, St. Louis, Mo., USA) containing rooting medium (half-strength MS medium and 2 mg $l^{-1}$ bialaphos) for 2-4 weeks at 25° C. under the above light conditions.

Plantlets were transferred from rooting medium to greenhouse potting mix (Sunshine mix number 1; Fison's, Canada) and were covered with beakers for the first few days after transplantation to prevent desiccation. Greenhouse day/night temperatures were 25±2/19° C. under a 16 h photoperiod with supplemental lights to provide 150 µmol $m^{-2}$ $s^{-1}$ light intensity. Herbicide resistance of primary transformants and progeny was tested by a leaf painting assay and/or spraying with a 1000-fold dilution of the commercial herbicide Glufosinate 200™ (AgrEvo, N.J., USA) containing 20% ammonium glufosinate.

Example 19

Detecting the Presence of SB109-TPSP and Bar Genes in Transformed Wheat Plants

A total of 35 putative transgenic wheat lines containing the plasmid pSB109-TPSP (that contains ABA stress-inducible promoter driving TPSP fusion gene) were successfully regenerated. One-month-old plants that were transferred to pots in the greenhouse were tested for phosphinothricin-based herbicide-resistance by painting the leaves using 0.5% Basta™ (Hoechst-Roussel, Agri-Vet Company, Somerville, N.J.). The leaves remained green in 57% transgenic plants and showed Basta-herbicide resistance, but in sensitive and non-transgenic control plants the leaves turned yellow. Integration of TPSP gene was confirmed by PCR analysis. Two sets of primers were designed from the TPSP gene (TPS1/TPS2, TPP1/TPP2) for PCR analysis of the genomic DNA. Out of the 20 plant DNA samples analyzed using either of the primer pairs, 9 plants showed the expected PCR product, confirming the presence of the transgene. Interestingly, most of the primary transformants appears to be phenotypically normal, unlike the other reports in dicots where multiple phenotypic alterations/pleiotropic effects were observed when trehalose gene(s) were expressed constitutively. This may be because of the regulated expression of trehalose biosynthetic gene in wheat.

Example 20

Transgenic Wheat Plants are Salt-Stress Tolerant

Transgenic plants that harbor the TPSP gene were analyzed for salt tolerance. Leaf segments of 0.5 cm long were cut from transgenic and non-transgenic plants and floated on different solutions of NaCl (200, 400, and 800 mM) with the upper surface of the discs in contact with the solution and kept under continuous white light for 72 hours. The leaf segments were then rinsed with distilled water and extracted with DMF (N,N'-dimethyl formamide) by grinding with 1 ml of DMF with a pestle and mortar. The homogenate and washing solution (1 ml) with the solvent were centrifuged at 2,500 rpm for 10 minutes. The pellet was then vortexed with 0.5 ml of solvent and the pooled supernatants were adjusted to a final volume of 3 ml. The absorption (A) of the leaf extract at 664 nm and 647 nm was measured with a spectrophotometer. Chl-a, Chl-b, and Chl-a+Chl-b concentrations (μg/ml) were calculated by the following equations: Chl-a=12.00 A-664 minus 3.11 A-647, Chl-b=20.78 A-664 minus 4.88 A-647, and Chl-a+Chl-b=17.67 A-647+7.12 A-664.

The results showed that leaf segments from the plants expressing the TPSP gene showed tolerance to NaCl with little or no significant bleaching, whereas that from the wild type showed extensive bleaching. Next, chlorophyll was isolated from control samples without salt treatment and samples after 72 hours of NaCl treatment. Chlorophyll content in plants in the absence of salt treatment was determined and set at 100. The results showed that in non-transgenic control plants, the chlorophyll content was decreased by approximately 15% at 400 mM salt, and approximately 25% at 800 mM NaCl. In contrast, in the case of transgenic lines, after salt stress the chlorophyll content was almost as high as that without salt stress.

Example 21

Transgenic Wheat Plants are Water-Stress Tolerant

A test for water-stress tolerance was carried out by measuring the electrolyte conductivity of the solution after soaking the leaf samples. Leaf segments were excised from plants. Duplicate samples (5 mg each) from each of two non-transgenic plants and each of four transgenic plants were excised from the plants. The leaf samples were placed on dry filter paper in 9-cm diameter Petri dishes and allowed to dry inside of a Laminar Flow Hood. Six hours later, the samples were transferred to different test-tubes that contained 2 ml distilled water. The test-tubes were subjected to vacuum three times at five-minute intervals at 60 psi to remove air bubbles adhered to the surface of leaves. The tubes then were shaken at 300 rpm for 2 hours in a slanted position. After shaking, the conductivity of the solution was measured using a conductivity meter (VWR International, West Chester, Pa.).

These results showed that the electrical conductivity of solutions used to soak leaves from non-transgenic plants was 5,400 μmho/mg leaf, whereas that from different transgenic lines was between 3,100 and 3,700 μmho/mg leaf. These results indicated that leaves from transgenic plants are less damaged by drying. In other words, leaves from transgenic plants are more tolerant to water stress.

Effect of Invention

As explained and demonstrated above, the present invention relates to a method for increasing resistance of monocot plants against abiotic stress which comprises a step of transforming monocot plants with a recombinant plasmid containing a fused gene (TPSP) of trehalose-6-phosphate synthetase (TPS) gene and trebalose-6-phosphate phosphatase (TPP) gene to express TPSP gene. The present invention increases the resistance of monocot plants against various stresses so that it can greatly contribute to the improvement of production and quality of valuable agricultural crops.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A method for increasing resistance of monocot plants against abiotic stress, which comprises a step of transforming a monocot plant with a recombinant plasmid containing a bifunctional fusion enzyme gene (TPSP) of trehalose-6 phosphate synthetase (TPS) gene and trehalose-6-phosphate phosphatase (TPP) gene to express a bifunctional TPSP fusion enzyme, thereby limiting trehalose-6-phosphate accumulation and enhancing accumulation of trehalose in the transformed monocot plants while maintaining normal plant growth and development characteristics, wherein expression of the bifunctional TPSP fusion enzyme is under control of a constitutive promoter.

2. The method for increasing resistance of monocot plants against abiotic stresses according to claim 1, wherein TPS gene and TPP gene are derived from *E. coli* or yeast.

3. The method for increasing resistance of monocot plants against abiotic stresses according to claim 1, wherein the monocot plant is rice, wheat, barley, or maize.

4. The method for increasing resistance of monocot plants against abiotic stresses according to claim 1, wherein the transformation is carried out according to *Agrobacterium*-mediated method.

5. The method for increasing resistance of monocot plants against abiotic stresses according to claim 1, wherein the abiotic stress is dehydration-stress, salt-stress or cold-stress.

6. A method for producing monocot plants having increased resistance against abiotic stresses, which comprises a step of transforming monocot plants or their ancestors with a recombinant plasmid containing a bifunctional fusion enzyme gene (TPSP) of trehalose-6-phosphate synthetase (TPS) gene and trehalose-6-phosphate phosphatase (TPP) gene to express a bifunctional TPSP fusion enzyme, thereby limiting trehalose-6-phosphate accumulation and enhancing accumulation of trehalose in the transformed monocot plants to enable growth without phenotypic growth alteration, wherein expression of the bifunctional TPSP fusion enzyme is under control of a constitutive promoter.

7. A method for generating a transgenic monocot plant comprising:
(a) constructing a (TPSP) fusion gene comprising a fused trehalose-6-phosphate synthetase (TPS) gene and trehalose-6-phosphate phosphatase (TPP) gene;
(b) transforming said TPSP fused gene into a recipient plant cell; and
(c) regenerating said plant cell into a mature plant, wherein said mature plant is a transgenic monocot plant that expresses, under control of a constitutive promoter, a bifunctional TPSP fusion enzyme.

8. The method of claim 7 wherein the transgenic monocot plant is selected from the group of monocot plants consisting of: rice, wheat, barley or maize.

9. A transgenic monocot plant produced by the method of claim 7, wherein the plant comprises said TPSP gene under the control of a constitutive promoter.

10. A transgenic monocot plant transformed with a nucleic acid encoding a bifunctional TPSP fusion enzyme for trehalose biosynthesis, under control of a constitutive promoter, that confers low temperature stress, salt stress, or water stress tolerance to the plant.

11. The transgenic monocot plant according to claim 10, wherein said monocot plant is selected from the group consisting of rice, wheat, maize (corn), barley, oat, rye, millet, and sorghum.

12. The transgenic monocot plant according to claim 11, wherein said monocot plant is a rice plant.

13. The transgenic monocot plant according to claim 11, wherein said monocot plant is a wheat plant.

14. The transgenic monocot plant according to claim 11, wherein said monocot plant is a maize (corn) plant.

15. A seed produced by the transgenic monocot plant of claim 10, wherein the seed comprises said nucleic acid encoding said bifunctional TPSP fusion enzyme for trehalose biosynthesis.

16. A seed, which upon germination, produces the transgenic monocot plant of claim 10.

17. A monocot plant cell or protoplast transformed with a nucleic acid encoding a bifunctional TPSP fusion enzyme for trehalose biosynthesis, under control of a constitutive promoter, that confers low temperature stress, salt stress, or water stress tolerance on a monocot plant regenerated from said monocot plant cell or protoplast.

18. The monocot plant cell or protoplast according to claim 17, wherein the monocot plant cell or protoplast is transformed with a trehalose-6-phosphate synthase/trehalose-6-phosphate phosphatase fusion gene.

19. The monocot plant cell or protoplast according to claim 17, wherein said monocot plant cell or protoplast further comprises a nucleic acid encoding a selectable marker.

20. A transgenic monocot plant regenerated from the monocot plant cell or protoplast of claim 17.

21. A seed produced by the transgenic monocot plant of claim 20 wherein the seed comprises said nucleic acid encoding said bifunctional TPSP fusion enzyme for trehalose biosynthesis.

22. A transgenic monocot plant regenerated from the monocot plant cell or protoplast of claim 18.

23. A seed produced by the transgenic monocot plant of claim 22 wherein the seed comprises a trehalose-6-phosphate synthase/trehalose-6-phosphate phosphatase fusion gene that expresses a bifunctional TPSP fusion enzyme.

24. A method of conferring low-temperature stress, water stress, or salt stress tolerance to a monocot plant comprising:
transforming a monocot plant cell or protoplast with a nucleic acid encoding a bifunctional TPSP fusion enzyme under control of a constitutive promoter for trehalose biosynthesis under conditions effective to confer low temperature stress, salt stress, or water stress tolerance to monocot plants produced from the monocot plant cell or protoplast.

25. The method according to claim 24, wherein said monocot plant cell or protoplast is derived from a plant selected from the group consisting of rice, wheat, maize (corn), barley, oat, rye, millet, and sorghum.

26. The method according to claim 25, wherein said monocot plant cell or protoplast is derived from a rice plant.

27. The method according to claim 25, wherein said monocot plant cell or protoplast is derived from a wheat plant.

28. The method according to claim 25, wherein said monocot plant cell or protoplast is derived from a maize (corn) plant.

29. The method according to claim 24, wherein the monocot plant cell or protoplast is transformed with a trehalose-6-phosphate synthase/trehalose-6-phosphate phosphatase fusion gene.

30. The method according to claim 24 further comprising:
regenerating the transformed monocot plant cell or protoplast to form a transgenic monocot plant.

31. A transgenic monocot plant produced by the method of claim 30, wherein the plant comprises said nucleic acid encoding said TPSP fusion enzyme for trehalose biosynthesis.

32. A seed produced by the transgenic monocot plant of claim 31 comprising said nucleic acid encoding said bifunctional TPSP fusion enzyme for trehalose biosynthesis.

* * * * *